US007537760B2

(12) United States Patent
Leone et al.

(10) Patent No.: US 7,537,760 B2
(45) Date of Patent: May 26, 2009

(54) MONOCLONAL ANTIBODIES RECOGNIZING BAG3 PROTEIN SEQUENCES AND THEIR USE IN DIAGNOSTIC AND THERAPY OF CELL DEATH-INVOLVING DISEASES

(76) Inventors: Arturo Leone, Via Domenico Fontana 134/4, 80128 Napoli (IT); Maria Caterina Turco, Via Errico 37, 83100 Avellino (IT)

( * ) Notice: Subject to any disclaimer, the term of this patent is extended or adjusted under 35 U.S.C. 154(b) by 458 days.

(21) Appl. No.: 10/500,665

(22) PCT Filed: Dec. 30, 2002

(86) PCT No.: PCT/EP02/14802

§ 371 (c)(1),
(2), (4) Date: Jun. 28, 2004

(87) PCT Pub. No.: WO03/055908

PCT Pub. Date: Jul. 10, 2003

(65) Prior Publication Data

US 2005/0176660 A1    Aug. 11, 2005

(30) Foreign Application Priority Data

Dec. 28, 2001    (EP)    ................................ 01830834

(51) Int. Cl.
*A61K 39/395* (2006.01)
*C07K 14/47* (2006.01)
*A61K 39/00* (2006.01)
*G01N 33/53* (2006.01)
*C07K 16/00* (2006.01)
*A61K 38/00* (2006.01)

(52) U.S. Cl. .............. 424/139.1; 424/141.1; 424/185.1; 436/548; 530/387.9; 530/326; 530/387.3; 435/7.1; 435/69.7

(58) Field of Classification Search ........................ None
See application file for complete search history.

(56) References Cited

U.S. PATENT DOCUMENTS 5,652,223 A * 7/1997 Kohn et al. .................... 514/44
6,696,558 B2 * 2/2004 Reed et al. ................. 536/23.5

FOREIGN PATENT DOCUMENTS

WO    WO/95/25125    * 9/1995
WO    WO/00/14106    * 3/2000

OTHER PUBLICATIONS

Schietinger et al., A Mutant Chaperone Converts a Wild-Type Protein into a Tumor-Specific Antigen. Science, 314, 304-308, 2006.*
Lobato et al., Intracellular Antibodies as Specific Reagents for Functional Ablation: Future Therapeutic Molecules. Curr. Mol. Med. 4, 519-528, 2004.*

Nicholson, "From Bench to Clinic with Apoptosis-Based Therapeutic Agents", *Nature*, vol. 407, Oct. 12, 2000.
Takayama et al., "Molecular Chaperone Targeting and Regulation by BAG Family Proteins", *Nature Cell Biology*, vol. 3, Oct. 2001.
Shinichi Takayama et al., "An Evolutionarily Conserved Family of Hsp70/Hsc70 Molecular Chaperone Regulators", *The Journal of Biological Chemistry*, vol. 274, No. 2, pp. 781-786, 1999.
Doong et al, CAIR-1/BAG-3 Forms an EGF-Regulated Ternary Complex with Phospholipase C-γ and Hsp 70/Hsc70, *Oncogene*, vol. 19, pp. 4385-4395 (2000).
Jeong-Hwa Lee et al., "Bis, a Bcl-2-binding Protein that Synergizes with Bcl-2 in Preventing Cell Death", Oncogene, 18, pp. 6183-6190 (1999).
Quan Liao, "The Anti-Apoptotic Protein BAG-3 is Overexpressed in Pancreatic Cancer and Induced by Heat Stress in Pancreatic Cancer Cell Lines", FEBS Letters, 503 pp. 151-157 (2001).
Antoku et al., "Isolation of Bcl-2 Binding Proteins that Exhibit Homology with BAG-2 and Suppresosor of Death Domains Protein", *Biochemical and Biophysical Research Communications*, 286, pp 1003-1010, (2001).
Renz et al., "Rapid Extracellular Release of Cytochrome c is Specific for Apoptosis and Marks Cell Death in Vivo", *Blood*, vol. 98, No. 5, (2001).
Kluck et al, "Cytochrome C Activation of CPP32-Like Proteolysis Plays a Critical Role in Xenopus Cell-Free Apoptosis System", *The Embo Journal*, vol. 16, No. 15, pp. 4639-4649, (1997).
Koopman et al., "Annexini V for Flow Cytometric Detection of Phosphatidylserine Expression on B Cells Undergoing Apoptosis", *Blood*, vol. 84, No. 5 (Sep. 1994).
Nicoletti et al., "A Rapid and Simple Method for Measuring Thymocyte Apoptosis by Propidium Iodide Staining and Flow Cytometry", *Journal of Immunological Methods*, 139, pp. 271-279, (1991).
Tassone et al., CD36 is Rapidly and Transiently Upregulated On Phytohemagglutinin (PHA)-Stimulated Peripheral Blood Lymphocytes. Analysis by a New Monoclonal Antibody (UN 7), *Tissue Antigens*, 51, pp. 671-675 (1998).
Romano et al., "Triggering of CD40 antigen Inhibits Fludarabine-Induced Apoptosis in B Chronic Lymphocytic Leukemia Cells", *Blood*, vol. 92, No. 3, pp. 990-995 (1998).
Stavros C. Manolagas, "Manipulating Programmed Cell Death for Better Living", Science's Stke, www.stke.org/cgi/content/full/OC_sigtrans; (2001).
Drissi, "C-Myc-Mediated Regulation of Telomerase Activity is Disabled in Immortalized Cells", *The Journal of Biological Chemistry*, vol. 276, No. 32, pp. 29994-30001 (2001).

(Continued)

*Primary Examiner*—Lorraine Spector
*Assistant Examiner*—Elly-Gerald Stoica
(74) *Attorney, Agent, or Firm*—Abelman, Frayne & Schwab

(57) ABSTRACT

The present invention provides BAG3 nucleotide and protein sequences to be used in research, diagnostics and therapy for modulation of cell survival and/or death, in particular in leukemias, other neoplasias and apoptosis-involving diseases. More particularly the invention refers to the use of specific antisense-based constructs and peptide-specific polyclonal and monoclonal antibodies in leukemias, other neoplasias and cell death-involving diseases.

5 Claims, 13 Drawing Sheets

OTHER PUBLICATIONS

Petit-Frere et al., "Apoptosis and Cytokine Release Induced by Ionizing or Ultraviolet B Radiation in Primary and Immortalized Human Keratinocytes" *Carcinogenesis*, vol. 21, No. 6, pp. 1087-1095, (2000).

Brezden et al., "Differential Cell Death in Iimmortalized and Non-Immortalized Cells at Confluency", *Oncogene*, 12, pp. 201-206, (1996).

Iordanov et al., "Differential Requirement for the Stress-Activated Protein Kinase/c-Jun $NH_2$—Terminal Kinase in RNA Damage-Induced Apoptosis in Primary and in Immortalized Fibroblasts", *Molecular Cell Biology Research Communications*, 4, pp. 122-128 (2000).

Marsden and Strasser, "Control of Apoptosis in the Immune System: Bcl-2, BH3-Only Proteins and More", *Annu. Rev. Immunol*, 21, pp. 71-105 (2003).

Roth et al., "Bag-1 and Bcl-2 Gene Transfer in Malignant Glioma: Modulation of Cell Cycle Regulation and Apoptosis", *Brain Pathology*, 10, pp. 223,-234 (2000).

Zong et al., "BH3-Only Proteins the Bind Pro-Survival Bcl-2 Family members Fail to Induce Apoptosis in the Absence of Bax and Bak", *Genes and Development*, 15, pp. 1481-1486, (2001).

Gewirtz, "Oligonucleotide Therapeutics: Clothing the Emperor", *Current Opinion in Molecular Therapeutics*, vol. 1, No. 3, (1999).

Opalinska et al, "Nucleic-Acid Therapeutics: Basic Principles and Recent Applications", *Nature Publishing Group*, vol. 1, pp. 503-514 (Jul. 2002).

Keah et al., "Direct Synthesis and Characterisation of Multi-Dendritic Peptides for Use as Immunogens", *J. Peptide Res*. 51, pp. 2-8, (1998).

Tam, "Synthetic Peptide Vaccine Design: Synthesis and Properties of a High-Density Multiple Antigenic Peptide System", *Proc. National Academy, Sciences*, vol. 85 pp. 5409-5413, (1988).

Ota et al., "Cellular Processing of a Multibranched Lysine Core with Tumor Antigen Peptides and Presentation of Peptide Epitopes Recognized by Cytotoxic T Lymphocytes on Antigen-Presenting Cells", *Cancer Research*, vol. 62, pp. 1471-1476, (2002).

\* cited by examiner

A

| | | | |
|---|---|---|---|
| R1 (alive) | 26.0 % | 23.1 % | 27.0 % |
| R2 (apoptotic) | 52.1 % | 55.5 % | 24.5 % |
| R3 (dead) | 17.7 % | 17.0 % | 45.5 % |

B

Annexin V

MONOCLONAL ANTIBODIES RECOGNIZING BAG3 PROTEIN SEQUENCES AND THEIR USE IN DIAGNOSTIC AND THERAPY OF CELL DEATH-INVOLVING DISEASES

FIELD OF THE INVENTION

The present invention provides BAG3 nucleotide and protein sequences to be used in research, diagnostics and therapy for cell death-involving diseases, and for modulation of cell survival and/or death.

More particularly the invention refers to the use of specific antisense-based constructs and peptide-specific polyclonal and monoclonal antibodies in leukemias, other neoplasias and cell death-involving diseases.

BACKGROUND

Cell death by apoptosis is largely responsible for control of tissue homeostastis, differentiative and immune processes. Alterations in the apoptosis program are implied in acute and chronic tissue damages (heart, kidney, brain or other tissue ischaemia, chronic degenerative disorders such as Parkinson's disease, amyotrophic lateral sclerosis and others, etc.), characterized by excessive apoptosis, and neoplastic, autoimmune and other diseases involving insufficient apoptosis. Furthermore, since antineoplastic compounds mainly act by inducing apoptosis in cancer cells, molecules involved in the apoptotic response determine neoplastic cell sensitivity or resistance to therapy. Biochemical components and/or regulators of the apoptotic pathways can be targets for modulating therapies, some of which have shown efficacy in preclinical models and are now in human clinical trials. Furthermore, apoptosis-involved molecules can represent diagnostic tools in a range of diseases and reagents for laboratory work (1).

BAG3 is member of the BAG protein family, involved in co-chaperone activity for intracellular protein folding (2). Although BAG3 displays homology with the other members of the BAG family in some portions, like the BAG domain, other parts of its nucleotide and protein sequences are unique (2-4). These BAG3-specific, unique portions have been utilised by us for the invention here described.

In the following there are reported the BAG3 nucleotide and peptide sequences; the underlined parts correspond to parts which are considered particularly relevant for the present invention.

BAG3 nucleotide sequence (SEQ ID NO: 1):
reference: NCBI PubMed. XM 055575
*Homo sapiens* BCL2-associated athanogene 3 (BAG3), mRNA
gi|16156810|ref|XM_055575.1|[16156810]

```
   1 gcggagctcc gcatccaacc ccgggccgcg gccaactttt ttggactgga ccagaagttt
  61 ctagccggcc agttgctacc tccctttatc tcctccttcc cctctggcag cgaggaggct
 121 atttccagac acttccaccc ctctctggcc acgtcacccc cgcctttaat tcataaaggt
 181 gccggcgcc ggcttcccgg acacgtcggc ggcggagagg ggcccacggc ggcggcccgg
 241 ccagagactc ggcgcccgga gccagcgccc cgcacccgcg ccccagcggg cagacccccaa
 301 cccagcatga gcgccgccac ccactcgccc atgatgcagg tggcgtccgg caacggtgac
 361 cgcgacccct tgcccccggg atgggagatc aagatcgacc cgcagaccgg ctggccttc
 421 ttcgtggacc acaacagccg caccactacg tggaacgacc cgcgcgtgcc ctctgagggc
 481 cccaaggaga ctccatcctc tgccaatggc ccttcccggg agggctctag gctgccgcct
 541 gctagggaag gccaccctgt gtaccccag ctccgaccag gctacattcc cattcctgtg
 601 ctccatgaag gcgctgagaa ccggcaggtg caccctttcc atgtctatcc ccagcctggg
 661 atgcagcgat tccgaactga ggcggcagca gcggctcctc agaggtccca gtcacctctg
 721 cggggcatgc cagaaaccac tcagccagat aaacagtgtg gacaggtggc agcggcggcg
 781 gcagcccagc ccccagcctc ccacggacct gagcggtccc agtctccagc tgcctctgac
 841 tgctcatcct catcctcctc ggccagcctg ccttcctccg gcaggagcag cctgggcagt
 901 caccagctcc cgcgggggta catctccatt ccggtgatac acgagcagaa cgttacccgg
 961 ccagcagccc agccctcctt ccaccaagcc cagaagacgc actacccagc gcagcagggg
1021 gagtaccaga cccaccagcc tgtgtaccac aagatccagg gggatgactg ggagcccgg
1081 cccctgcggg cggcatcccc gttcaggtca tctgtccagg gtgcatcgag ccgggagggc
1141 tcaccagcca ggagcagcac gccactccac tcccctcgc ccatccgtgt gcacaccgtg
1200 gtcgacaggc ctcagcagcc catgacccat cgagaaactg cacctgtttc ccagcctgaa
1261 aacaaaccag aaagtaagcc aggcccagtt ggaccagaac tccctcctgg acacatccca
1321 attcaagtga tccgcaaaga ggtggattct aaacctgttt cccagaagcc cccacctccc
```

```
-continued
1381 tctgagaagg tagaggtgaa agttccccct gctccagttc cttgtcctcc tcccagccct
1441 ggcccttctg ctgtcccctc ttcccccaag agtgtggcta cagaagagag ggcagccccc
1501 agcactgccc ctgcagaagc tacacctcca aaaccaggag aagccgaggc tcccccaaaa
1561 catccaggag tgctgaaagt ggaagccatc ctggagaagg tgcaggggct ggagcaggct
1621 gtagacaact ttgaaggcaa gaagactgac aaaaagtacc tgatgatcga agagtatttg
1681 accaaagagc tgctggccct ggattcagtg gaccccgagg gacgagccga tgtgcgtcag
1741 gccaggagag acggtgtcag gaaggttcag accatcttgg aaaaacttga acagaaagcc
1801 attgatgtcc caggtcaagt ccaggtctat gaactccagc ccagcaacct tgaagcagat
1861 cagccactgc aggcaatcat ggagatgggt gccctggcag cagacaaggg caagaaaaat
1921 gctggaaatg cagaagatcc ccacacagaa acccagcagc cagaagccac agcagcagcg
1981 acttcaaacc ccagcagcat gacagacacc cctggtaacc cagcagcacc gtagcctctg
2041 ccctgtaaaa atcagactcg gaaccgatgt gtgctttagg gaattttaag ttgcatgcat
2101 ttcagagact ttaagtcagt tggttttttat tagctgcttg gtatgcagta acttgggtgg
2161 aggcaaaaca ctaataaaag ggctaaaaag gaaaatgatg cttttcttct atattcttac
2221 tctgtacaaa taaagaagtt gcttgttgtt tcagaagttt aaccccgttg cttgttctgc
2281 agccctgtct acttgggcac cccaccacc tgttagctgt ggttgtgcac tgtcttttgt
2341 agctctggac tggaggggta gatggggagt caattaccca tcacataaat atgaaacatt
2401 tatcagaaat gttgccattt taatgagatg attttcttca tctcataatt aaaatacctg
2461 actttagaga gagtaaaatg tgccaggagc cataggaata tctgtatgtt ggatgacttt
2521 aatgctacat ttt
```

BAG3 aminoacidic sequence (SEQ ID NO: 2):
reference: NCBI PubMed. XM 055575
*Homo sapiens* BCL2-associated athanogene 3 (BAG3), mRNA
gi|16156810|ref|XM_055575.1|[16156810]

MSAATHSPMMQVASGNGDRDPLPPGWEIKIDPQTGWPFFVDHNSRTTTWNDP

RVPSEGPKETPSSANGPSREGSRLPPAREGHPVYPQLRPGYIPIPVLHEGAENR

QVHPFHVYPQPGMQRFRTEAAAAAPQRSQSPLRGMPETTQPDKQCGQVAAAA

AAQPPASHGPERSQSPAASDCSSSSSSASLPSSGRSSLGSHQLPRGYISIPVIHE

QNVTR

PAAQPSFHQAQKTHYPAQQGEYQTHQPVYHKIQGDDWEPRPLRAASPFRSSVQ

GASSREGSPARSSTPLHSPSPIRVHTVVDRPQQPMTHRETAPVSQPENKPESKP

GPVGPELPPGHIPIQVIRKEVDSKPVSQKPPPPSEKVEVKVPPAPVPCPPPSPGPS

AVPSSPKSVATEERAAPSTAPAEATPPKPGEAEAPPKHPGVLKVEAILEKVQGLEQ

AVDNFEGKKTDKKYLMIEEYLTKELLALDSVDPEGRADVRQARRDGVRKVQTILEK

LEQKAIDVPGQVQVYELQPSNLEADQPLQAIMEMGAVAADKGKKNAGNAEDPHT

ETQQPEATAAATSNPSSMT

DTPGNPAAP

BAG3 protein is known to be expressed in some cell lines, such as HeLa and A2058, and, as far as normal primary human cells are concerned, in skeletal muscle, heart, ovary and other types of normal cells (2-5). BAG3 expression has also been detected in human pancreas tumour cells (6).

BAG3 expression had not been reported in other types of primary normal or neoplastic cells before the results here reported for the first time.

Some findings describe that transfection of cells of the human cell line HeLa (5) or of the murine cell line 32D (7) with BAG3 hyperexpressing constructs can modestly increase cell apoptosis induced by Bax microinjection or via Fas (5), or by IL-3 deprivation (7), respectively.

Generically antibodies for BAG3 have been described in WO00/14106 and WO95/25125, however there has not been characterized any immunogenic site specific for them. Ref.s 4-6 describe polyclonal antibodies specific for the carbossi-terminal region of BAG3 protein starting from amino acid 306 specifically. Liao describes a rabbit polyclonal anti-BAG3 antibody against the 196 amino acids of the C-terminal portion of BAG3. Lee describes a polyclonal antibody against the amino acid region encompassing the portion 306-575. Dong describes a polyclonal antibody against the two amino acid regions 2 and 8.

Patent abstract of Japan publication 10327872 describes uses of BAG3 for diagnosis, prophylaxis and therapy of pathologies relating to apoptosis, however there has not been characterized any immunogenic site or any specific antibody, moreover test, in particular in humans, are absent.

Before results here reported for the first time, BAG3 expression had not been proved to influence apoptosis in human primary cells, either normal, neoplastic or affected by other types of pathologies. Furthermore, BAG3 downmodulation by reagents, such as oligonucleotides, that can be used in primary cells, and its effects on cell apoptosis had never been reported.

SUMMARY OF THE INVENTION

The present invention refers to BAG3 protein (SEQ ID NO: 2) and corresponding nucleotide sequence (SEQ ID NO: 1) and parts of them (indicated by underlining inside the above mentioned long sequences).

Objects of the present invention are therefore the uses of BAG3 polypeptides and polynucleotides codifying it and parts of them in research, diagnostics and therapy for modulating primary cell survival and/or death, particularly in human leukemias and other neoplasias or cell death-involving diseases.

There are considered within the scope of the invention in that BAG3-related: sense or antisense oligonucleotides; monoclonal or polyclonal antibodies that specifically recognise one or more BAG3-specific epitopes: in particular:

| SEQ ID NO 15: | DRDPLPPGWEIKIDPQ; |
| SEQ ID NO 16: | SSPKSVATEERAAPS; |
| SEQ ID NO 17: | DKGKKNAGNAEDPHT; |
| SEQ ID NO 18: | NPSSMTDTPGNPAAP; | primers for PCR; nucleotide sequences for analysis of DNA or RNA; the polypeptide and polynucleotide sequences encoding them, including recombinant DNA molecules, cloned genes or degenerate variants thereof, especially naturally occurring variants such as allelic variants.

Reagents and compositions for the uses described in the present invention additionally include vectors, including expression vectors, viruses, etc., containing BAG3-specific sequences; cells genetically engineered to contain such sequences and cells genetically engineered to express such sequences. Reagents additionally include the complement of any of the nucleotide sequences recited above.

Compositions for the uses described in the present invention may further comprise an acceptable carrier, such as pharmaceutically acceptable carrier.

BAG3-based uses described in the present invention include also methods for preventing, treating or ameliorating a medical condition, which comprises administering to a human or other animal subject a therapeutically effective amount of a composition comprising BAG3-based reagents. Examples are methods for preventing, treating or ameliorating: acute or chronic tissue damages, such as heart, kidney, brain or other organ ischaemia, HIV-related damage of brain or other tissues, skeletal muscle disorders, transplantation rejection; chronic degenerative disorders such as Parkinson's disease, amyotrophic lateral sclerosis and others, etc.; and neoplastic, autoimmune and other diseases involving excessive or defective apoptosis; tissue repair or wound healing, treatment of surgical incisions, and ulcers, such as stomach or diabetic ulcers; etc.

BAG3-based uses described in the present invention relate also to reagents and methods for detecting the presence of BAG3 nucleotide sequence or protein, or parts of them. Such methods can, for example, be utilised as part of prognostic and diagnostic and/or prognostic evaluation of disorders as recited above and for the identification of subjects exhibiting a predisposition to such conditions. Furthermore, the invention include BAG3-related uses for evaluating the efficacy of drugs, and monitoring the progress of patients, involved in clinical trials for the treatment of disorders as recited above.

BAG3-related uses of the present invention include also reagents and/or methods for the identification of compounds that modulate the expression or the activity of BAG3. Such reagents or methods can be utilised, for example, for the identification of compounds that can ameliorate symptoms of disorders as recited above. Such methods can include, but are not limited to, assays for identifying compounds and other substances that interact with (e.g., bind to) BAG3 protein or nucleotide sequence or parts of them.

The invention also includes methods for detecting the presence of the nucleotide sequence SEQ ID NO: 1 or of the protein SEQ ID NO: 2 or parts of them in a sample, in particular at least a part identified as SEQ ID NO: 3, 4, 5, 6, 7, 8, 15, 16, 17, 18; said method comprising the steps of: contacting the sample with a compound that binds to and forms a complex with the nucleotide or the protein in sufficient conditions to form the complex, and detecting said complex. The expert in the field is able to select the suitable conditions to perform the method.

The invention also includes methods for detecting a compound that binds to the protein SEQ ID NO: 2 or parts of it in a sample, in particular at least a part identified as SEQ ID NO: 4, 6, 8, 15, 16, 17, 18; said method comprising the steps of: contacting the compound with the protein or its part/s in sufficient conditions to form the complex compound/protein or its part/s, and detecting said complex. The expert in the field is able to select the suitable conditions to perform the method.

The invention also includes methods for the treatment of disorders as recited above which may involve the administration of such compounds to individuals exhibiting symptoms or tendencies related to disorders as recited above. In addition, the invention encompasses methods for treating diseases or disorders as recited above by administering compounds and other substances that modulate the overall activity of BAG3 and related molecules. Compounds and other substances can effect such modulation either on the level of gene expression or protein activity.

The diagnostic, prognostic or therapeutic compositions for the BAG3-related use related to the present invention are also presently valuable for veterinary applications. Particularly domestic animals and thoroughbred horses, in addition to humans, are desired patients for such applications.

The invention further refers to a kit for identification and diagnosis comprising the polyclonal or monoclonal antibodies identified in the following description or nucleotide sequence SEQ ID NO: 1 or the protein SEQ ID NO: 2 or parts of them, in particular at least a part identified as SEQ ID NO: 3, 4, 5, 6, 7, 8, 15, 16, 17, 18; or the antisense and nonsense oligos identified as SEQ ID NO: 9, 10, 11, 12, 13, 14, or functionally equivalents of the above identified sequences.

BAG3-based uses described in the present invention relate also to reagents and/or methods and/or kits for laboratory work or research.

Further objects of the invention will become evident from the following detailed description of the invention.

Table 1 describes the effect of anti-BAG3 antisense oligodeoxynucleotides on apoptosis in cells of the human osteosarcoma line SAOS.

Table 2 describes the protective effect of BAG3 hyperexpression on stress-induced apoptosis in the human cell line 293.

Table 3 describes the effect of BAG3 hyperexpression on the growth of human neoplastic (osteosarcoma) cells xenografted in nude mice.

Table 4 shows the results of the ELISA tests performed to verify the binding of hybridoma mother clone supernatants to MAP-BAG3 constructs.

Figure 13:
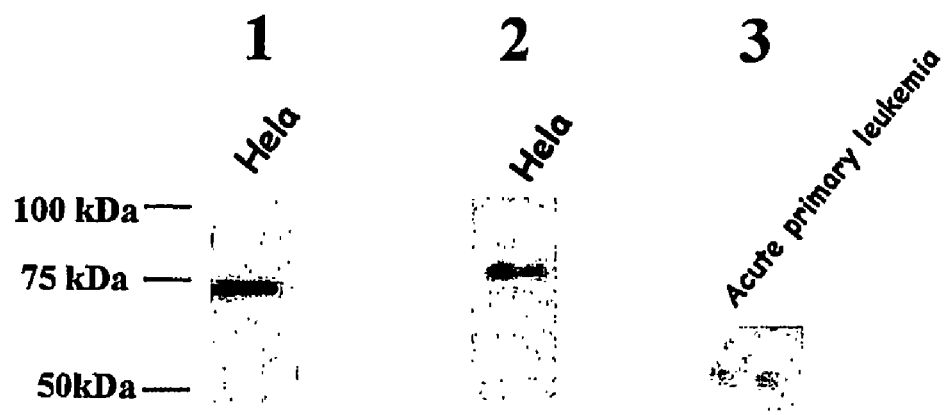
Figure 13:
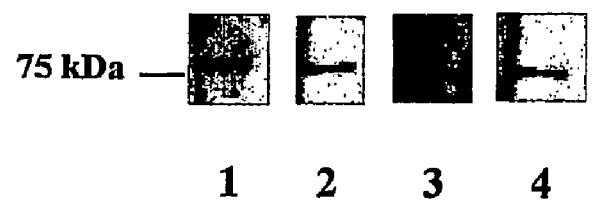

FIG. 13 shows the binding of the polyclonal antibodies AC-BAG3-2 and AC-BAG3-1 to lysates from HeLa or primary leukemia cells (A) and of the hybridoma mother clones (AC-1, AC-2, AC-3, AC4) supernatants to cell lysates from HeLa cells (B), as detected by Western blotting.

DETAILED DESCRIPTION OF THE INVENTION

The polynucleotidic and aminoacidic fragments that are considered particularly relevant for the present invention and are comprised inside SEQ ID NO: 1 and 2, are indicated in the following, such sequences are relevant because are specific of BAG3 and not shared with any other known sequence of other BAG genes or proteins:

```
SEQ ID NO: 3:
gcggagctcc gcatccaacc ccgggccgcg gccaactttt ttggactgga ccagaagttt ctagccggcc agttgctacc tcccttatc tcctccttcc cctctggcag cgaggaggct atttccagac acttccaccc ctctctggcc acgtcacccc cgcctttaat tcataaaggt gcccggcgcc ggcttcccgg acacgtcggc ggcggagagg ggcccacggc ggcggcccgg ccagagactc ggcgcccgga gccagcgccc cgcacccgcg ccccagcggg cagaccccaa cccagcatga gcgccgccac ccactcgccc atgatgcagg tggcgtccgg caacggtgac

SEQ ID NO: 4:
MSAATHSPMMQVASGNGDRDPLPPGWEIKIDPQTG

SEQ ID NO: 5:
gtgcc ctctgagggc cccaaggaga ctccatcctc tgccaatggc ccttcccggg agggctctag gctgccgcct gctagggaag gccaccctgt gtaccccag ctccgaccag gctacattcc cattcctgtg ctccatgaag gcgctgagaa ccggcaggtg caccctttcc atgtctatcc ccagcctggg atgcagcgat tccgaactga ggcggcagca gcggctcctc agaggtccca gtcacctctg cggggcatgc cagaaaccac tcagccagat aaacagtgtg gacaggtggc agcggcggcg gcagcccagc ccccagcctc ccacggacct gagcggtccc agtctccagc tgcctctgac tgctcatcct catcctcctc
```

-continued

```
ggccagcctg ccttcctccg gcaggagcag cctgggcagt caccagctcc cgcggggta catctccatt ccggtgatac acgagcagaa cgttacccgg ccagcagccc agccctcctt ccaccaagcc cagaagacgc actacccagc gcagcagggg gagtaccaga cccaccagcc tgtgtaccac aagatccagg gggatgactg ggagcccggg cccctgcggg cggcatcccc gttcaggtca tctgtccagg gtgcatcgag ccgggagggc tcaccagcca ggagcagcac gccactccac tccccctcgc ccatccgtgt gcacaccgtg gtcgacaggc ctcagcagcc catgacccat cgagaaactg cacctgtttc ccagcctgaa aacaaaccag aaagtaagcc aggcccagtt ggaccagaac tccctcctgg acacatccca attcaagtga tccgcaaaga ggtggattct aaacctgttt cccagaagcc cccacctccc tctgagaagg tagaggtgaa agttccccct gctccagttc cttgtcctcc tcccagccct ggcccttctg ctgtcccctc ttcccccaag agtgtggcta cagaagagag ggcagccccc agcactgccc ctgcagaagc tacacctcca aaaccaggag aagccgaggc tcccccaaaa catccaggag
```

SEQ ID NO: 6:
NDPRVPSEGPKETPSSANGPSREGSRLPPAREGHPVYPQLRPGYIPIPVLHEGA

ENRQVHPFHVYPQPGMQRFRTEAAAAAPQRSQSPLRGMPETTQPDKQCGQVA

AAAAAQPPASHGPERSQSPAASDCSSSSSSASLPSSGRSSLGSHQLPRGYISIP

VIHEQNVTRPAAQPSFHQAQKTHYPAQQGEYQTHQPVYHKIQGDDWEPRPLRA

ASPFRSSVQGASSREGSPARSSTPLHSPSPIRVHTVVDRPQQPMTHRETAPVS

QPENKPESKPGPVGPELPPGHIPIQVIRKEVDSKPVSQKPPPPSEKVEVKVPPAP

VPCPPPSPGPSAVPSSPKSVATEERAAPSTAPAEATPPKPGEAEAPPKHPGVLK

VEAILEKVQGLEQAVDNFEG

SEQ ID NO: 7
```
attgatgtcc caggtcaagt ccaggtctat gaactccagc ccagcaacct tgaagcagat cagccactgc aggcaatcat ggagatgggt gccgtggcag cagacaaggg caagaaaaat gctggaaatg cagaagatcc ccacacagaa acccagcagc cagaagccac agcagcagcg acttcaaacc ccagcagcat gacagacacc cctggtaacc cagcagcacc gtagcctctg ccctgtaaaa atcagactcg gaaccgatgt gtgctttagg gaattttaag ttgcatgcat ttcagagact ttaagtcagt tggtttttat tagctgcttg gtatgcagta acttgggtgg aggcaaaaca ctaataaaag ggctaaaaag gaaaatgatg cttttcttct atattcttac tctgtacaaa taaagaagtt gcttgttgtt tcagaagttt aacccgttg
cttgttctgc agccctgtct acttgggcac ccccaccacc tgttagctgt ggttgtgcac tgtcttttgt agctctggac tggaggggta gatggggagt caattcccca tcacataaat atgaaacatt tatcagaaat gttgccattt taatgagatg attttcttca tctcataatt aaaatacctg actttagaga gagtaaaatg tgccaggagc cataggaata tctgtatgtt ggatgacttt aatgctacat ttt
```

SEQ ID NO: 8:
ELQPSNLEADQPLQAIMEMGAVAADKGKKNAGNAEDPHTETQQPEATAAATSN

PSSMTDTPGNPAAP

The experiments performed in our laboratories indicate for the first time that specific antisense oligonucleotides are able to modulate, in human primary cells and human cell lines, the levels of BAG3 protein; these antisense oligos modulate also the survival and/or death, either spontaneous or in response to therapy, of human primary cells and human cell lines. Experiments with primary cells, that are the target of diagnostic and therapeutic applications, are particularly relevant, and the results were not predictable from data obtained with cell lines, since stable cell lines and primary cells are differently sensitive to modulators of cell survival and/or death (14-18); furthermore, the effect of BAG3 protein downmodulation on cell survival and/or death, either in cell lines or primary cells, were not reported before, nor were predictable from data concerning BAG3 hyperexpression, since several examples have been reported, in which the overexpression of a protein (i.e. Bcl-2 family proteins) can protect cells from pro-apoptotic insults, but its downmodulation does not stimulate apoptosis (19-21); finally, BAG3 downmodulation has been obtained with specific antisense oligonucleotides, that can be used for research, diagnosis and/or therapy, and their effectiveness was not predictable before the experimental work, since not all antisense oligonucleotides against a specific mRNA display comparable activities when introduced in a cell, and furthermore some antisense molecules can exert unpredicted, not desired effects, such as citotoxicity (22-23).

BAG3 modulation is able to influence the development of a human tumour in vivo; these results are necessary for in vivo applications, are absolutely required for proving the biological activity of a gene and/or protein and the effects of its modulation in pluricellular organisms, and cannot be extrapolated in this respect from results in vitro (1).

Based on the apoptosis-modulating effect of the antisense according to the invention, a panel of polyclonal and monoclonal antibodies raised against peptide constructs (MAP-BAG3-peptides) has been designed to: map different BAG3 epitopes and/or domains; relate them to the functional activity of BAG3 (i.e., modulation of cell survival); relate them to specific biochemical interaction with molecular partners and/or formation of complexes; target them to neutralize (antagonistic antibodies) or trigger (agonistic antibodies) BAG3 functional activity.

Identification of BAG3 expression in human primary leukemia cells and effectiveness of specific antisense oligonucleotides in modulating BAG3 levels and cell survival and/or death.

We analysed by PCR the expression of BAG3 mRNA in primary cells from B-CLL patients. BAG3 mRNA was detectable in such cells, and its levels appeared to be enhanced by treatment with a chemotherapeutic compound, fludarabine phosphate (FIG. 1, A panel).

To explore the levels of BAG3 protein, we first used a polyclonal antibody according to the teaching of the patent appl WO95/25125. Such antibody appeared to bind with a low avidity BAG3 protein from primary leukemic cells and had therefore to be used in condition of high resolution (high antibody concentration, long incubation times, etc.). Therefore we decided to produce novel polyclonal antibodies by using a different approach, i.e. using a Multiple Antigen Peptide (MAP) prepared in a single synthesis by the solid-phase method described in ref. 24-26. Such approach allows to improve the immunogenecity of the antigenic peptides and obtain particularly efficient antibodies. (24-26) This is of high relevance for detecting proteins expressed in low amounts, as usually happens for many relevant proteins in physiologic or pathologic conditions in primary cells. The kind of MAP used, here as for the subsequent production of hybridomas (see below), was an octa-branching MAP consisting of a core matrix made up of three levels of lysine and eight amino terminals for anchoring peptide antigens. In this case, we used the peptide NPSSMTDTPGNPAAP (SEQ ID NO: 18), corresponding to the last 15 aminoacids of the carboxyterminal region of BAG3 protein. For obtaining policlonal antibodies, two rabbits were immunised with 4 boosts (a boost every 2 week) of MAP-BAG3-4 (400 micrograms for each boost); the serum was finally tested against MAP-BAG3-4 in ELISA test and verified to be positive. We named the two polyclonal antibodies, obtained from the two rabbits, AC-BAG3-1 and AC-BAG3-2: both recognised the carboxyterminal region of BAG3 protein and were efficient in detecting BAG3 protein, either in Western blotting or in immunofluorescence, in primary cells, as shown in FIGS. 1, 2, 11, 13.

Figure 1:
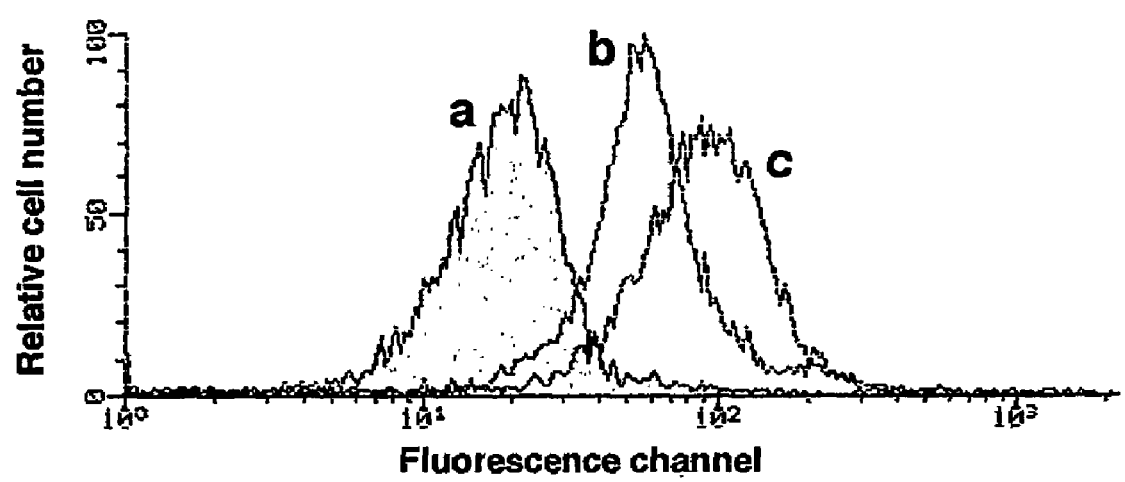
FIG. 1 shows the expression of BAG3 mRNA (A panel) and protein (B panel) in primary cells from leukemia patients.

With this BAG3-specific antibodies we analysed by immunofluorescence the expression of BAG3 protein, that was detectable in primary cells from B-CLL patients and whose levels appeared to be enhanced by treatment fludarabine (FIG. 1, B panel). In a comprehensive investigation of 18 different B-CLL specimens, 13 displayed detectable levels of BAG3 protein, and in 11 of these BAG3 levels were upregulated by treatment with fludarabine.

These findings for the first time demonstrate that BAG3 expression can be detected in primary leukemic cells and modulated by therapy. Such results disclose a diagnostic and/or prognostic use, not shown before, of BAG3-detecting reagents in leukemias.

To be able to modulate BAG3 expression, we constructed the following BAG-3-based antisense oligonucleotides:

```
antisense 1:  TGCATCATGG GCGAGTGGGT (SEQ ID NO: 9)
              GGCGG, antisense 2:  GCTCATGCTG GGTTGGGGTC (SEQ ID NO: 10)
              TG, antisense 3:  ATTAAAGGCG GGGGTGACGT (SEQ ID NO: 11)
              GG,
``` and control nonsense:

```
nonsense 1:
TTATATTCTATTATATTTATGAACTCC,      (SEQ ID NO: 12)

nonsense 2:
CCTCGTAACCACCG ACCTCAAT,          (SEQ ID NO: 13)

nonsense 3:
GCTTATGGAG GATTGAGGTT GG.         (SEQ ID NO: 14)
```

Other oligonucleotides can be constructed, functionally analogues to the ones mentioned before, in particular the oligonucleotides can be constructed based on sequences indicated as SEQ ID NO: 3, 5, 7.

There are within the scope of the present invention the nucleotide and peptide sequences that show functional equivalence with the ones identified in the description or that have a homology of at least 75%, preferably at least 80% homology, more preferably at least 90% homology, more preferably at least 95% homology, even more preferably at least 98% homology to at least one of the sequences mentioned in the description.

Figure 2:
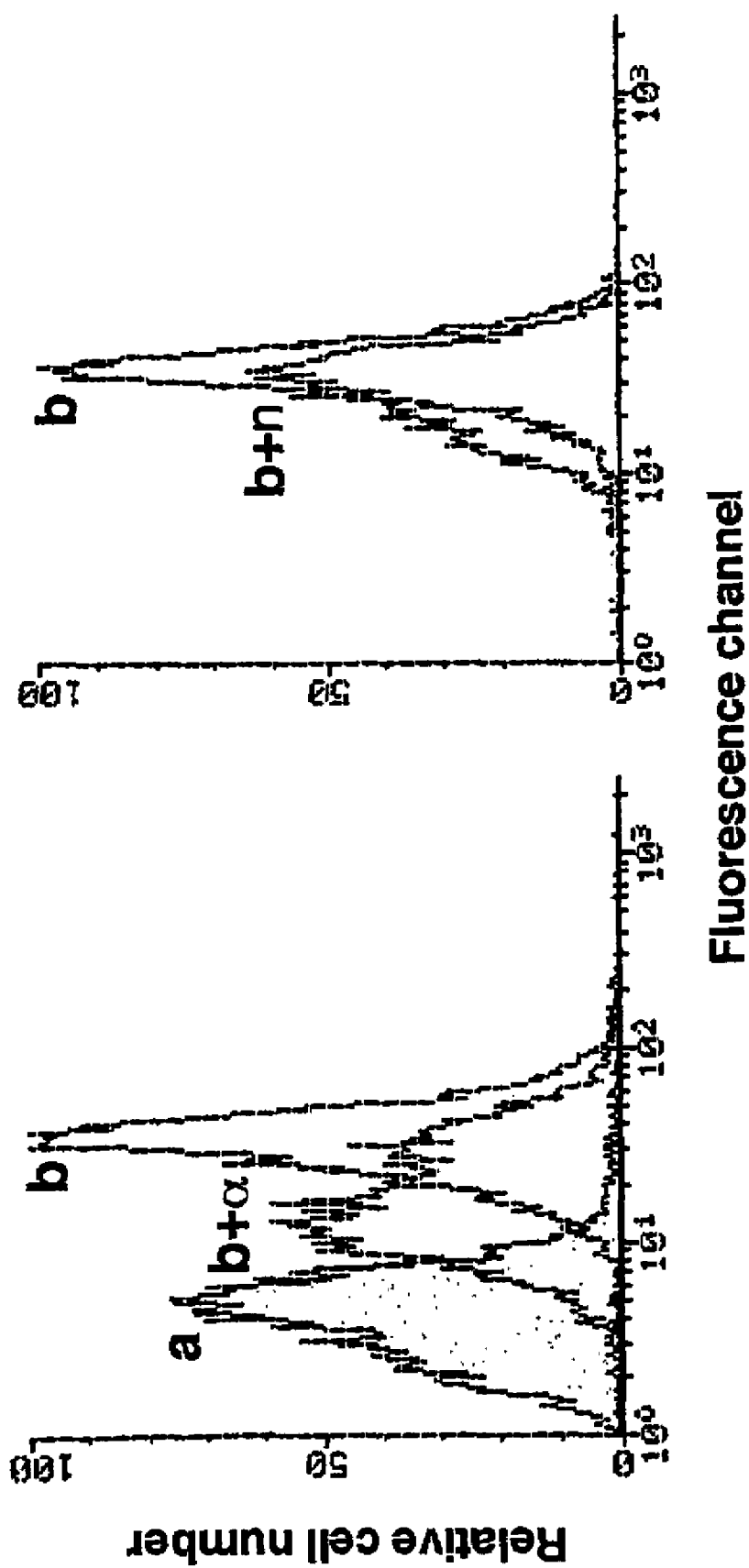
FIG. 2 shows the BAG3 downmodulation ability of anti-BAG3 antisense oligodeoxynucleotides in primary cells from leukemia patients.

Administering of antisense, but not of nonsense, oligonucleotides to human primary leukemic cells ex vivo resulted in a downmodulation of BAG3 protein levels. Representative results are shown in FIG. 2; analogous results were obtained in experiments with three different B-CLL specimens. These findings disclose the use, not shown before, of BAG3 antisense oligonucleotides for affecting BAG3 protein levels in primary (in this case neoplastic, and specifically leukemic) cells.

Figure 6:
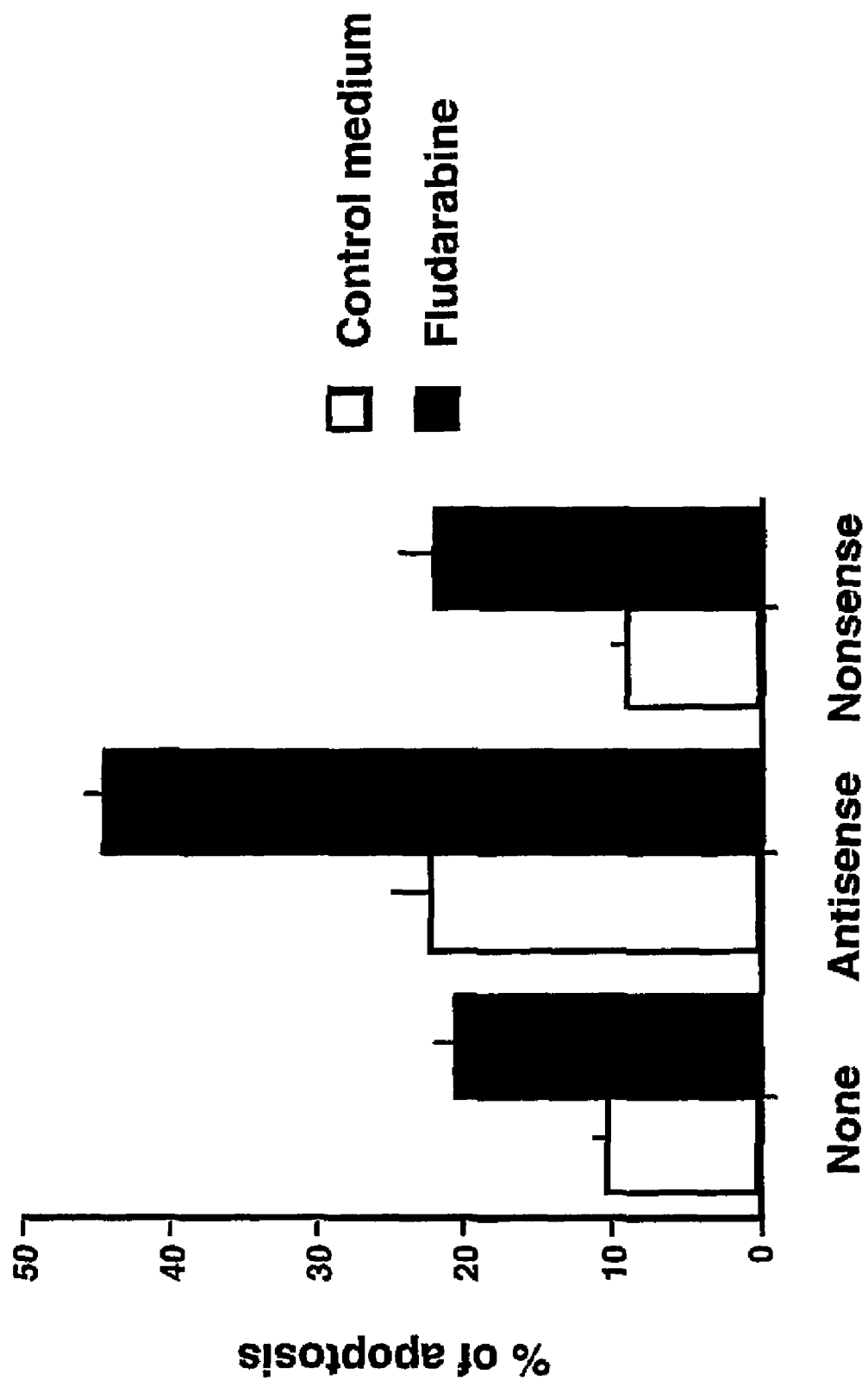
FIG. 6 shows the stimulation of primary B-CLL (B chronic lymphocytic leukemia) cell apoptosis by anti-BAG3 antisense oligodeoxynucleotides.
Figure 7:
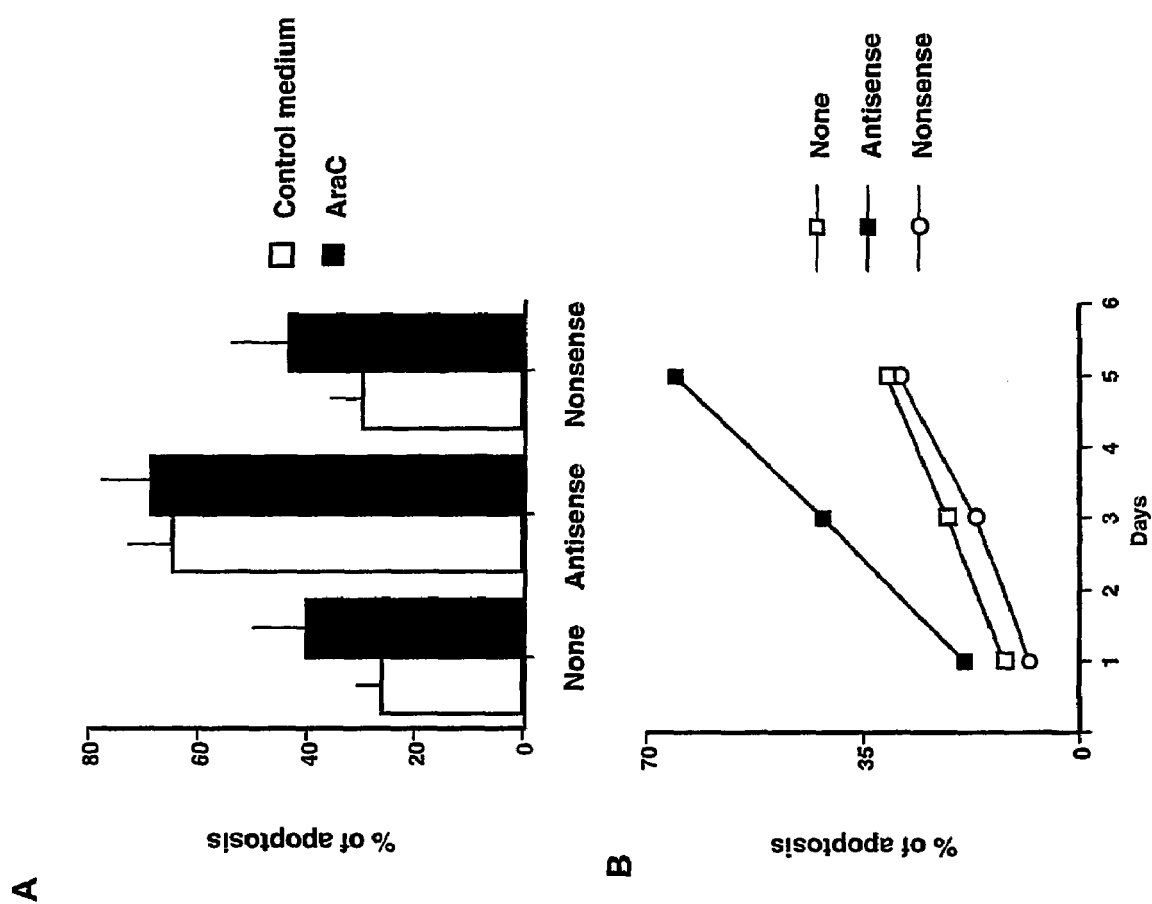
FIG. 7 shows the stimulation of primary ALL (acute lymphoblastic leukemia) cell apoptosis by anti-BAG3 antisense oligodeoxynucleotides.

We then analysed whether antisense oligonucleotides, by downmodulating BAG3 protein levels, could affect cell apoptosis. Primary cells from leukemia patients were incubated with or without antisense or control oligonucleotides and/or fludarabine, and different events of apoptosis: mitochondrial cytochrome c release (8), caspase 3 activation (9), annexin V binding (10) and appearance of hypodiploid elements (11) were analysed. A comprehensive analysis of 15 B-CLL samples indicated that administering of antisense, but not of nonsense, oligonucleotides to the cells resulted in stimulation of mitochondrial cytochrome c release (FIG. 3), caspase activity (FIG. 4), annexin V binding (FIG. 5) and appearance of hypodiploid elements (FIG. 6). Apoptosis stimulation was even more amplified by the addition of fludarabine (FIG. 6). Furthermore, in 4 of 4 ALL specimens analysed, the pro-apoptotic effect of the antisense oligonucleotides alone was particularly remarkable, since the percentage of hypodiploid elements reached >60% of the cells (similar to the value obtained with the chemotherapeutic compound AraC) (FIG. 7).

Therefore we demonstrate for the first time that downmodulation of BAG3 protein levels by administration of BAG3 antisense oligonucleotides to different types of human primary leukemia cells can stimulate apoptosis. The pro-apoptotic effect is remarkable when the antisense oligonucleotides are administered alone and can be synergic with that of different chemotherapeutic compounds.

These findings disclose the possible use, not shown before, of BAG3-modulating reagents, such as antisense oligonucleotides, for modulating survival and/or death in human primary cells, in this case neoplastic, and specifically leukemic. They also indicate the possible use of such reagents in synergy with other drugs.

Figure 9:
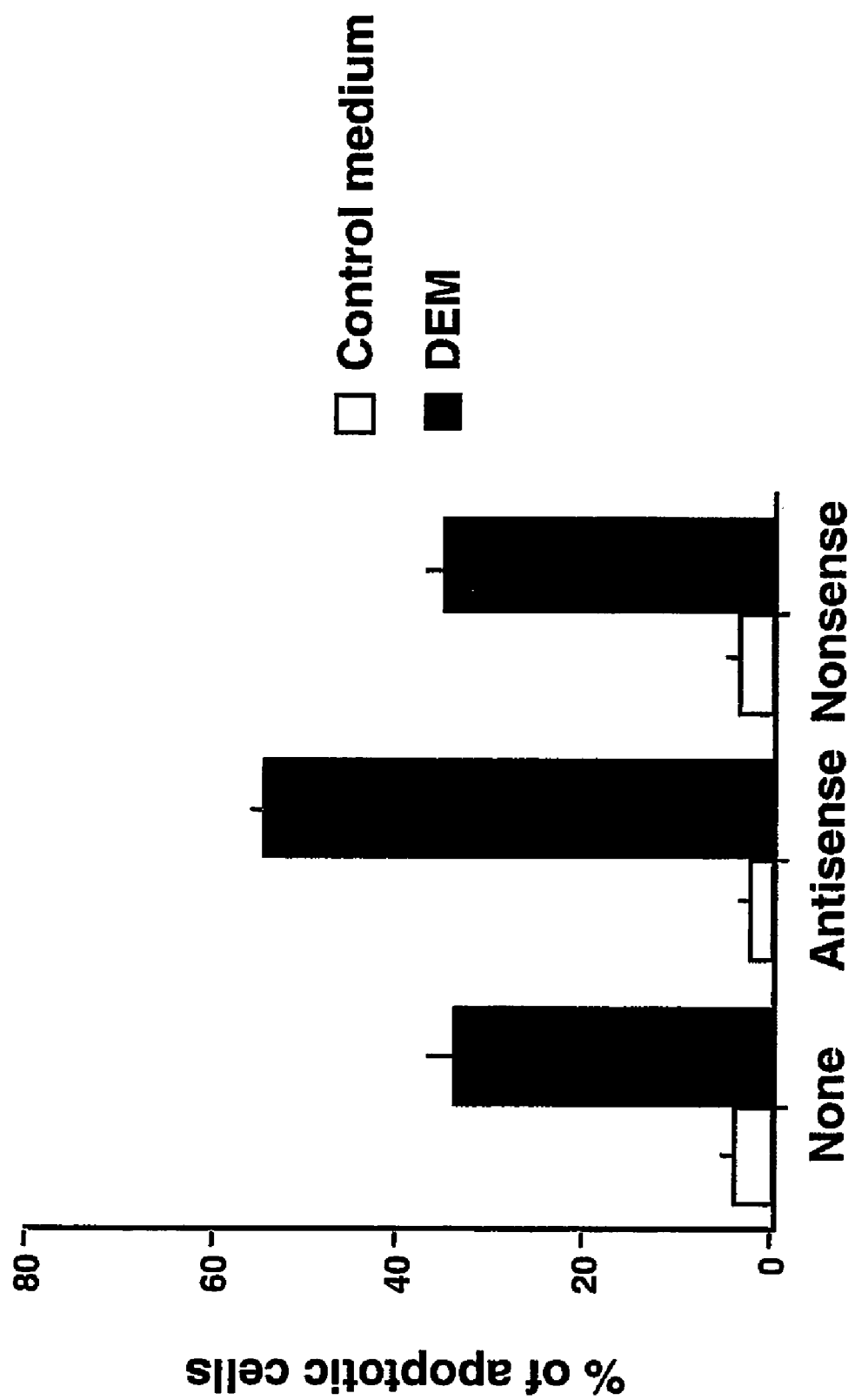
FIG. 9 shows the stimulation of stress-induced apoptosis in cells of the human myeloid leukemia line U937 by anti-BAG3 antisense oligodeoxynucleotides.
Figure 10:
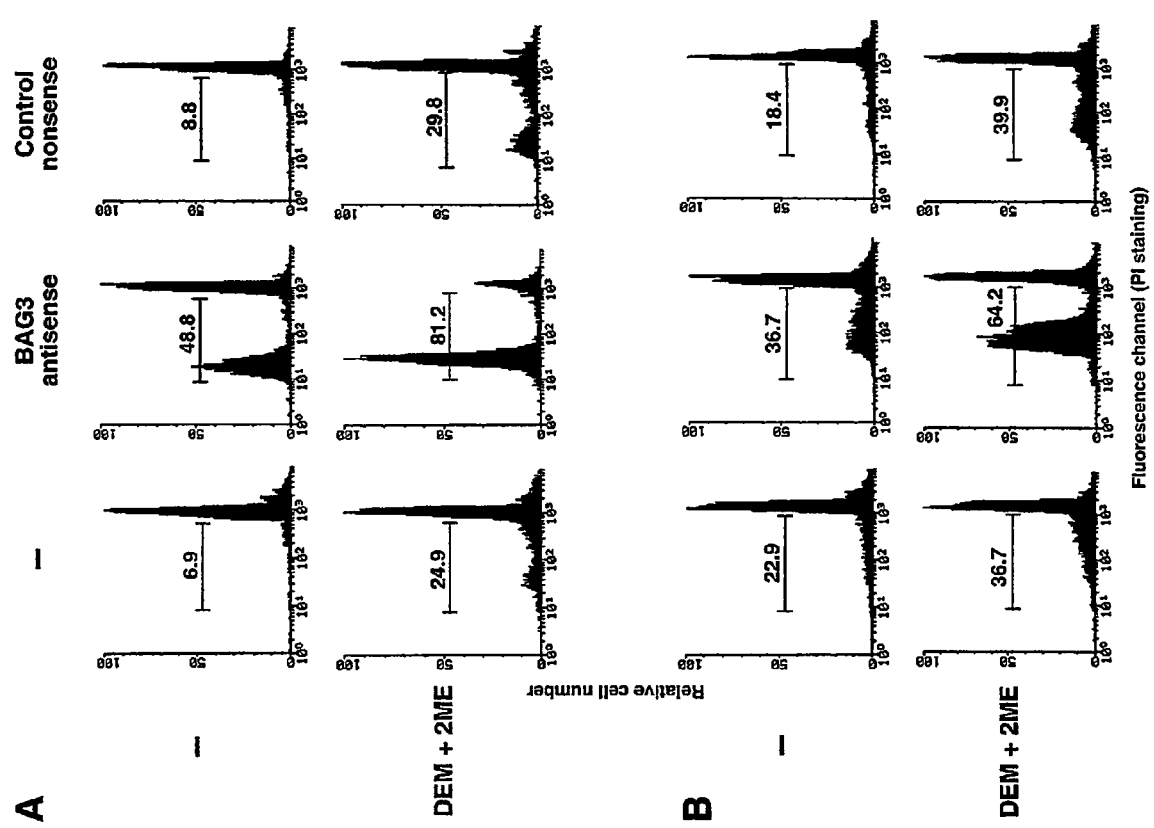
FIG. 10 shows the stimulation of stress-induced apoptosis in human normal peripheral blood primary lymphocytes (A panel) or monocytes (B panel) by anti-BAG3 antisense oligodeoxynucleotides.

Additional results were obtained by using human cells of different types: osteosarcoma cells of the SAOS line, in which we detected a remarkable pro-apoptotic effect of the antisense oligonucleotides alone (table 1); and myeloid cells of the U937 line, in which BAG3 antisense could enhance apoptosis induced by stress (FIG. 9). Particularly, the enhancement of stress-induced apoptosis in U937 cells suggested to us to verify whether BAG3-based reagents could interfere also with stress effects in human primary cells. Therefore we administered the antisense or control oligonucleotides to human normal peripheral blood lymphocytes or monocytes ex vivo, treated with the stress inducers diethylmaleate (DEM) and 2-Methoxymethylestradiol (2-ME). Antisense, but not control, oligo, highly enhanced cell apoptosis in these cells (FIG. 10). These findings for the first time demonstrate that stress effects on human primary cells (in this case, normal cells, and specifically lymphocytes and monocytes from peripheral blood) can be modulated by BAG3-based reagents.

We investigated whether protection from cell death could be obtained with BAG3-based reagents. Therefore we transfected 293 cells with a BAG3-hyperexpressing construct and verified the effect on stress-induced apoptosis. Transfection with the BAG3 construct resulted in protection from stress-induced apoptosis (table 2).

The above described results indicate for the first time that: 1) BAG3 is expressed in human primary leukemic cells; 2) BAG3 protein levels, and spontaneous or therapy-induced death of human primary cells, can be modulated by using specific antisense oligonucleotides.

It is worthy of note that this is the first reported observation that specific BAG3 antisense oligonucleotides are able to enhance human primary cell apoptosis. It has been previously shown that the overexpression of BAG-3 in transfected cell lines could partially protect them from apoptosis induced via Fas or growth factor deprivation (5,7). Our invention was not predictable from such previous observation, for three reasons: 1) stable cell lines and primary cells are differently sensitive to modulators of cell survival and/or death (14-18); 2) several examples have been reported, in which the overexpression of a protein (i.e. Bcl-2 family proteins) can protect cells from pro-apoptotic insults, but its downmodulation does not stimulate apoptosis (19-21); 3) not all antisense oligonucleotides against a specific mRNA display comparable activities when introduced in a cell; furthermore, some antisense molecules can exert unpredicted, not desired effects, such as citotoxicity (22-23). Therefore, the properties of the specific antisense oligonucleotide sequences used by us could not be predicted before our experimental work.

This is the first reported observation of BAG3 expression in human primary leukemic cells. This was not predictable from previous results described in stable cell lines and primary cells other than leukemia cells. Indeed: a) cell lines are no longer subjected to the environmental influences of a pluricellular organisms, and furthermore and more importantly are selected for their survival in culture: therefore they usually differ in gene expression and/or levels of particular proteins from primary cells, even when belonging to the same type; b) different cell types, either from lines or primary cells, differ in gene expression and/or levels of particular proteins (14-19).

Finally, since we have demonstrated that the modulation of BAG3 protein levels can modulate cell survival and/or death in primary cells, also polynucleotides and corresponding codified polypeptides indicated as SEQ ID NO: 2, 3, 4, 5, 6, 7, 8, 15, 16, 17, 18 and constructs comprising them dare una definizione minima di costrutto (hyperexpressing constructs, either in plasmid or other vectors; naked DNA; etc.) that positively modulate such levels are relevant in this functional activity. Particularly, we have demonstrated that the functional effect is specific of BAG3 and not shared with other BAG proteins, and therefore the SEQ ID NO 3, 5 and 7 are identified as particularly relevant for the functional effect (i.e., modulation of cell survival and/or death).

Demonstration that BAG3 Modulation can Influence Tumour Development in vivo.

Hyperexpression of BAG3 had been reported to suppress apoptosis in cell lines in vitro, since the overexpression of BAG-3 in transfected cell lines could partially protect them from apoptosis induced via Fas or growth-factor deprivation (5,7).These results did not allow to predict the effect of BAG3 hyperexpression on tumour development in vivo. Indeed, tumours in vivo are subjected to the environmental influences of a pluricellular organisms, and molecules that have a specific activity in vitro can fail their effects or show different activities in vivo: therefore effects in vivo cannot be extrapolated from results in vitro and a specific experimental work in vivo is required (1). We transfected cells of the human osteosarcoma cell line Saos with a BAG3-overexpressing plasmid vector and obtained a mass culture of stably transfected cells. Wild type cells, the transfected culture and a control, void vector-transfected culture were injected in three different sites (back, left and right sides) in nude mice. Wild type and control cells did not give rise to any tumour, while BAG3-hyperexpressing cells developed detectable tumours, demonstrating that BAG3 modulation can influence the development of a tumour in vivo (table 3).

Design and Construction of a Panel of Polyclonal and Monoclonal Antibodies

The antibodies were raised against peptide constructs (MAP-BAG3-peptides) to recognise and/or trigger the following defined BAG3 epitopes and/or domains

```
SEQ ID NO 15:      DRDPLPPGWEIKIDPQ;

SEQ ID NO 16:      SSPKSVATEERAAPS;

SEQ ID NO 17:      DKGKKNAGNAEDPHT;

SEQ ID NO 18:      NPSSMTDTPGNPAAP
``` of functional importance in human primary cells and other cell types of different origins.

The above described antisense oligonucleotides were all able to downmodulate the levels of BAG3 protein. This is relevant for the consequent modulation of cell death, here reported for the first time.

The functional activity of BAG3 in modulating cell survival and/or death can rely on biochemical interactions of specific BAG3 epitopes and/or domains indicated as SEQ ID NO 16, 16, 17, 18 with molecular partners involved in survival/death pathway (2). Indeed, a variety of such partners have been detected for BAG proteins in general and BAG3 in particular (2-5); such interactions can potentially involve different parts of the molecule, such as, in addition to the BAG domain, the WW domain, the SER-rich part, the PRO-rich part, etc. (described in 2-5). In view of the functional activity of BAG3 in modulating cell survival, it is important to be able to map different BAG3 epitopes and/or domains: this can allow to: 1) relate such epitopes to the functional activity of BAG3; 2) identify the site(s) of interactions with known partners, as well as new sites of interactions with still undescribed partners; 3) interfere with the formation of complexes with molecular partners; 4) block or mimic the interaction with these partners, leading to modulation of BAG3 functional activity.

To produce effective tools able to explore the above mentioned issues, we decided to obtain polyclonal and monoclonal antibodies against specific peptides representing spatially distinct portions of BAG3 protein. Such polyclonal and monoclonal antibodies are desirable to: map different BAG3 epitopes and/or domains; relate them to the functional activity of BAG3 (i.e., modulation of cell survival); relate them to specific biochemical interaction with molecular partners and/or formation of complexes; target them to neutralize (antagonistic antibodies) or trigger (agonistic antibodies) BAG3 functional activity.

We identified the following, spatially distinct BAG3-derived peptides:

| | |
|---|---|
| (SEQ ID NO 15): | DRDPLPPGWEIKIDPQ; |
| (SEQ ID NO 16): | SSPKSVATEERAAPS; |
| (SEQ ID NO 17): | DKGKKNAGNAEDPHT; |
| (SEQ ID NO 18): | NPSSMTDTPGNPAAP. |

Such peptide corresponded to one we used for raising the polyclonal antibodies (see above). Its use is here aimed at obtaining monoclonal antibodies against the carboxyterminal part of BAG3 (indeed, only polyclonal antibodies against such part have been so far: see ref. 4-6). Furthermore, its use is in addition, and not alternative, to that of the other three peptides (SEQ ID N. 15, 16 and 17).

We used these peptides to obtain separate monoclonal antibodies against each one of the four peptides.

All four peptides are specific of BAG3 protein and are not shared with other any protein, including other BAG proteins.

For immunising the animals, we decided to use MAPs (Multiple Antigenic Peptides) (24-26). As described in the previous section, the construction of MAPs allows to significantly enhance the immunogenicity of the antigenic peptides and to obtain particularly efficient antibodies. This is of relevance for detecting proteins expressed in low amounts, as usually happens for many relevant proteins in physiologic or pathologic conditions in primary cells. Following this approach, we obtained the following unique map constructs:

```
MAP-BAG3-1:
nh2-                                    (SEQ ID NO 15)
DRDPLPPGWEIKIDPQ-MAP containing MAP-BAG3-2:
nh2-SSPKSVATEERAAPS-MAP containing (SEQ ID NO 16)

MAP-BAG3-3:
nh2-DKGKKNAGNAEDPHT-MAP containing (SEQ ID NO 17)

MAP-BAG3-4:
nh2-NPSSMTDTPGNPAAP-MAP containing (SEQ ID NO 18)
```

The production of the polyclonal antibodies has been described above. In this respect, as well as for the production of monoclonal antibodies, MAP constructs are to be considered unique and different from the simple peptides alone, since their ability to elicit immunogenic responses in the animal is different form that of the peptides used alone (24-26).

Monoclonal antibodies (not yet reported in literature) were highly required, either in general because of the high specificity and homogeneity of such reagents, but also in particular in view of our results demonstrating the apoptosis-modulating properties of BAG3 protein in primary cells. Indeed BAG proteins, including BAG3, interact with several molecular partners (2-5,7), and monoclonal antibodies are required to map the protein epitopes involved in interacting with specific partners, thereby leading to effects on cell survival and/or death. Furthermore, monoclonal antibodies can display agonistic or antagonistic properties respect to the biological functions of a protein, and this is of relevance for the potential application in modulating BAG3 activity in cell survival and/or death.

For obtaining the monoclonal antibodies, we followed standard procedures, already performed in our laboratory (12). Specifically:

nine Balb/c female mice of 4 weeks were immunised with 4 boosts (a boost every 2 week) of the four MAP-BAG3 together (200 micrograms each, i.e. 800 micrograms of total protein/mouse/boost). Spleens were then obtained and fused with myeloma cells (NS0) to obtain monoclonal antibodies mother clones. These were tested against each of the four MAP-BAG3 in ELISA test (see table 4).

We produced:

nine murine monoclonal antibody mother clones (AC-1, AC-2, AC-3, AC-4, AC-5, AC-6, AC-7, AC-8, AC-9) obtained from mice immunised with the four MAP-BAG3 together. The nine mother clones are presently being subcloned to obtain hybridomas against each one of the four MAP-BAG3 constructs. The ELISA tests of the antibodies produced by the nine mother clones are presented in table 4. Importantly, the ELISA tests demonstrate that the mother clones contains hybridomas able to recognise each one of the four MAP-BAG3 used. Therefore, the nine mother clones already contain several specific hybridomas, each of whom can recognise one of the four epitopes represented in the MAPs and can hence be used to map one BAG3 epitope and interfere with its functional interactions and activities; the monospecific hybridomas are presently being separated by subcloning procedures.

The detection, by Western blot analysis, of BAG3 protein in lysates from the cell line HeLa and primary leukemia cells are shown in FIG. 13. Specifically:

the antibodies from the nine monoclonal mother clones did recognise the four MAP-BAG3 constructs in ELISA test (table 4);

four of them have been as yet tested, with positive results, in Western blot with HeLa lysates (FIG. 13, B panel).

In conclusion, the nine murine monoclonal antibody mother clones (AC-1, AC-2, AC-3, AC4, AC-5, AC-6, AC-7, AC-8, AC-9) contain hybridomas specific for each one of the four MAP-BAG3 constructs, and are able to identify spatially distinct parts of BAG3 molecule, in particular the mother clone AC-1 was n°PD02009 deposited on the 17 Dec. 2002 at the Centro Biotecnologie Avanzate di Genova They can therefore be used to: map different BAG3 epitopes and/or domains; relate them to the functional activity of BAG3 (i.e., modulation of cell survival); relate them to specific biochemical interaction with molecular partners and/or formation of complexes; target them to neutralize (antagonistic antibodies) or trigger (agonistic antibodies) BAG3 functional activity.

The original features of these results are:

the downmodulating effect of antisense oligos constitutes the original rationale, not predictable before, leading to the necessity of mapping and triggering BAG3 epitopes that mediate the mechanism of apoptosis modulation. This constituted the premise for the production of a panel of antibodies raised against different region of BAG3 protein;

a panel of nine monoclonal-producing mother clones (AC-1; AC-2; AC-3; AC-4; AC-5; AC-6; AC-7; AC-8; AC-9) have been obtained and can be used to: map different BAG3 epitopes and/or domains; relate them to the functional activity of BAG3 (i.e., modulation of cell survival); relate them to specific biochemical interaction with molecular partners and/or formation of complexes; target them to neutralize (antagonistic antibodies) or trigger (agonistic antibodies) BAG3 functional activity;

two polyclonal antibodies (AC-BAG3-1 and AC-BAG3-2), able to reveal the presence of BAG3 protein in human primary leukemias and its modulated expression of BAG3 protein by specific antisense oligodeoxynucleotides, have been obtained.

Within the scope of the present invention, BAG3-protein, the corresponding polynucleotide, corresponding parts of them and corresponding antisense oligonucleotides can be used for research, diagnostic and therapeutic purposes for example in leukemias, other neoplasias and cell death-involving diseases, and for modulation of cell survival and/or death. BAG3-based reagents include in a non-limitative manner, oligonucleotides, primers, probes, (poly)peptides or protein, polyclonal or monoclonal antibodies, etc., and any other reagent able to detect or modulate BAG3 expression.

Findings illustrated in the present invention and obtained with the described BAG3-based reagents could be obtained with modified reagents with equivalent activities. These latter are therefore considered equivalent to those illustrated in the present invention.

Particularly, as far as protein or its parts, or peptides, are concerned, are considered equivalent:

naturally occurring (poly)peptides or proteins, that are (poly)peptides or proteins produced by cells that have not been genetically engineered and specifically contemplates various (poly)peptides or proteins arising from post-translational modifications of the (poly)peptide or protein including, but not limited to, acetylation, carboxylation, glycosylation, phosphorylatioh, lipidation and acylation;

derivatives, that are (poly)peptides or proteins chemically modified by such techniques as ubiquitination, labeling (e.g., with radionuclides, fluorochromes or various enzymes), pegylation (derivatization with polyethylene glycol) and insertion or substitution by chemical synthesis of amino acids such as ornithine, which do not normally occur in human proteins;

recombinant variants, that are (poly)peptides or proteins differing from naturally occurring (poly)peptides or proteins by amino acid insertions, deletions, and substitutions, created using recombinant DNA techniques; Guidance in determining which amino acid residues may be replaced, added or deleted without abolishing activities of interest, such as cellular trafficking, may be found by comparing the sequence of the particular polypeptide with that of homologous peptides and minimizing the number of amino acid sequence changes made in regions of high homology.

Preferably, amino acid substitutions are the result of replacing one amino acid with another amino acid having similar structural and/or chemical properties, i.e., conservative amino acid replacements. Amino acid substitutions may be made on the basis of similarity in polarity, charge, solubility, hydrophobicity, hydrophilicity, and/or the amphipathic nature of the residues involved. For example, nonpolar (hydrophobic) amino acids include alanine, leucine, isoleucine, valine, proline, phenylalanine, tryptophan, and methionine; polar neutral amino acids include glycine, serine, threonine, cysteine, tyrosine, asparagine, and glutamine; positively charged (basic) amino acids include arginine, lysine, and histidine; and negatively charged (acidic) amino acids include aspartic acid and glutamic acid. The variation allowed may be experimentally determined by systematically making insertions, deletions, or substitutions of amino acids in a polypeptide molecule using recombinant DNA techniques and assaying the resulting recombinant variants for activity.

Alternatively, where alteration of function is desired, insertions, deletions or non-conservative alterations can be engineered to produce altered (poly)peptides or proteins. Such alterations can, for example, alter one or more of the biological functions or biochemical characteristics. For example, such alterations may change (poly)peptide or protein characteristics such as ligand-binding affinities, interchain affinities, or degradation/turnover rate. Further, such alterations can be selected so as to generate (poly)peptides or proteins that are better suited for expression, scale up and the like in the host cells chosen for expression. For example, cysteine residues can be deleted or substituted with another amino acid residue in order to eliminate disulfide bridges.

Substantially equivalent can be either nucleotide or amino acid sequences, for example a mutant sequence, that varies from a reference sequence by one or more substitutions, deletions, or additions, the net effect of which does not result in an adverse functional dissimilarity between the reference and subject sequences. Typically, such a substantially equivalent sequence varies from the reference one by no more than about 20%, i.e. the number of individual residue substitutions, additions, and/or deletions in a substantially equivalent sequence, as compared to the corresponding reference sequence, divided by the total number of residues in the substantially equivalent sequence is about 0.2 or less. Such a sequence is said to have 80% sequence identity to the listed sequence. In one embodiment, a substantially equivalent, mutant, sequence of the invention varies from a listed sequence by no more than 10% (90% sequence identity); in a variation of this embodiment, by no more than 5% (95% sequence identity); and in a further variation of this embodiment, by no more than 2% (98% sequence identity). Compared to aminoacidic identity, substantially equivalent nucleotide sequence(s) of the invention can have lower percent sequence identities, taking into account, for example, the redundancy or degeneracy of the genetic code. For the purposes of the present invention, sequences having substantially equivalent biological activity and substantially equivalent expression characteristics are considered substantially equivalent. For the purposes of determining equivalence, truncation of the mature sequence (e.g., via a mutation, which creates a spurious stop codon) should be disregarded.

Nucleic acid sequences encoding such substantially equivalent sequences, sequences of the recited percent identities can routinely be isolated and identified via standard hybridization procedures well known to those of skill in the art.

Where desired, an expression vector may be designed to contain a signal or leader sequence which will direct the polypeptide through the membrane of a cell. Such a sequence may be naturally present or provided from heterologous protein sources by recombinant DNA techniques.

Recombinant variants encoding these same or similar (poly)peptides or proteins may be synthesized or selected by making use of the redundancy in the genetic code. Various codon substitutions, such as the silent changes, which produce various restriction sites, may be introduced to optimize cloning into a plasmid or viral vector or expression in a particular prokaryotic or eukaryotic system. Mutations in the polynucleotide sequence may be reflected in the polypeptide or domains of other peptides added to the polypeptide to modify the properties of any part of the polypeptide, to change characteristics such as ligand-binding affinities, interchain affinities, or degradation/turnover rate.

Parts of the BAG3-related nucleotide or aminoacid sequence may be fused to carrier molecules such as immunoglobulins for many purposes, including increasing the valency of protein binding sites.

Reagents based on species homologs of BAG3 are considered equivalent respect to the uses illustrated in the present invention.

The sequences falling within the scope of the present invention are not limited to the specific sequences herein described, but also include allelic variations thereof. The present invention will be illustrated by the following examples, figures and tables which are not to be considered as limiting the scope of the invention.

DETAILED DESCRIPTION OF THE FIGURES AND TABLES

FIG. 1—Expression of BAG3 mRNA and protein in primary cells from leukemia patients. Leukemic cells were isolated from B-CLL patients' peripheral blood specimens by centrifugation through Ficoll-Hypaque (13) and cultured for 24 hours in RPMI 1640 medium supplemented with 10% fetal calf serum (10% FCS-RPMI), without or with fludarabine phosphate. A panel: cell mRNA was the extracted and BAG3 expression was verified by PCR (GAPDH expression is shown for comparative purpose); B panel: cells were permeabilised and analysed by indirect immunofluorescence with the polyclonal antibody AC-BAG3-1. A=control rabbit Ig; b=cells incubated with control medium and analysed with anti-BAG3; c=cells incubated with fludarabine and analysed with anti-BAG3.

FIG. 2—Downmodulation of BAG3 protein levels by anti-BAG3 antisense oligodeoxynucleotides. Leukemic cells were isolated from B-CLL patients' peripheral blood specimens by centrifugation through Ficoll-Hypaque and cultured for 20 hours without (b) or with BAG3 antisense (b+α) or control nonsense (b+ν) phosphorothioate oligodeoxynucleotides (5 microM) described in the text. Then cells were permeabilised and analysed by indirect immunofluorescence with the polyclonal antibody AC-BAG3-1. a=control rabbit Ig.

Figure 3:
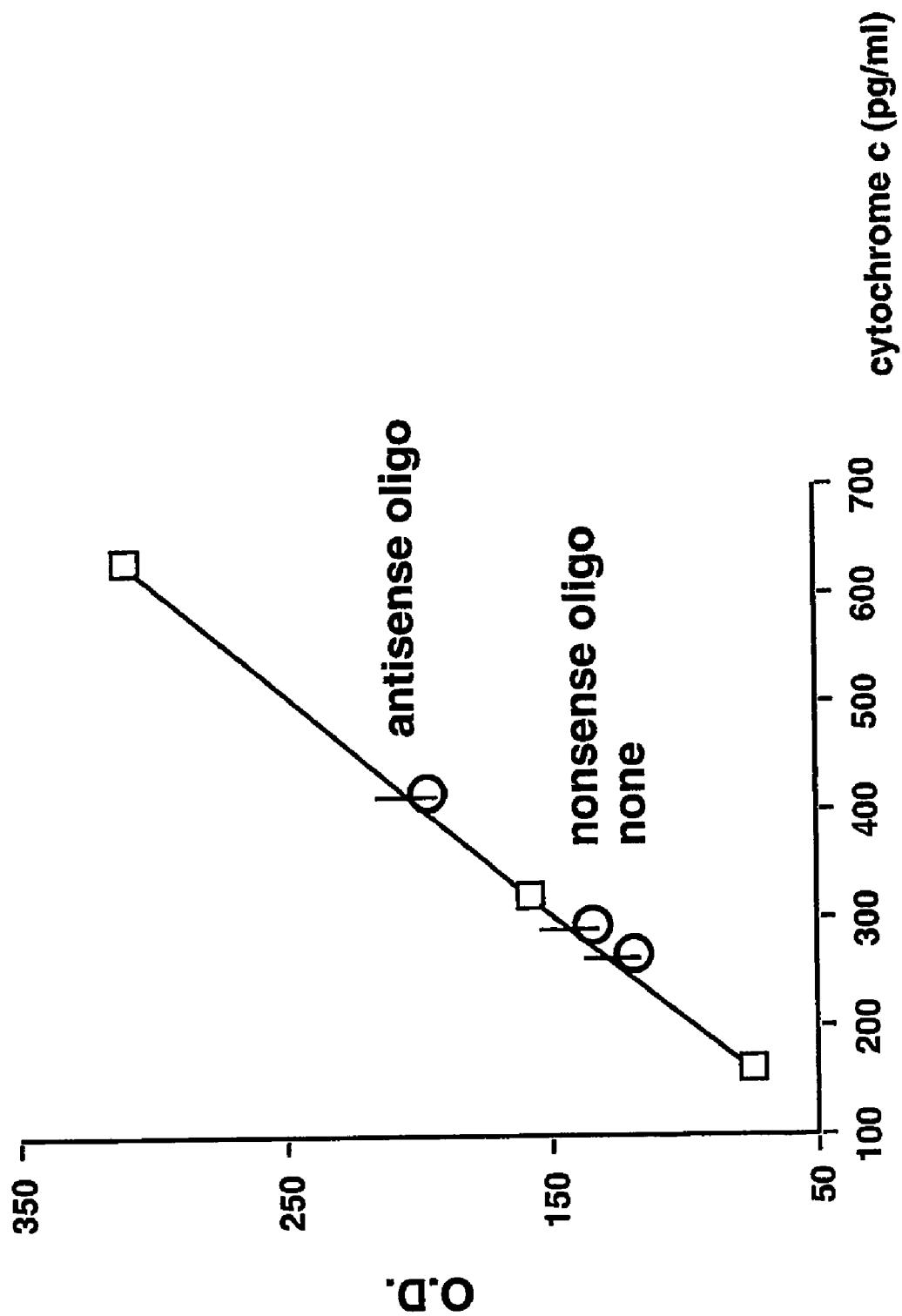
FIG. 3 shows the stimulation of mitochondrial cytochrome c release by anti-BAG3 antisense oligodeoxynucleotides in primary cells from leukemia patients.

FIG. 3—Effect of anti-BAG3 antisense oligodeoxynucleotides on mitochondrial cytochrome c release in B-CLLs. Leukemic cells were isolated from B-CLL patients' peripheral blood specimens by centrifugation through Ficoll-Hypaque and cultured for the indicated times without or with the BAG3 antisense or control nonsense phosphorothioate oligodeoxynucleotides (5 microM) described in the text. Then cell extracts were obtained and mitochondrial cytochrome c release was analysed according to ref. 8.

Figure 4:
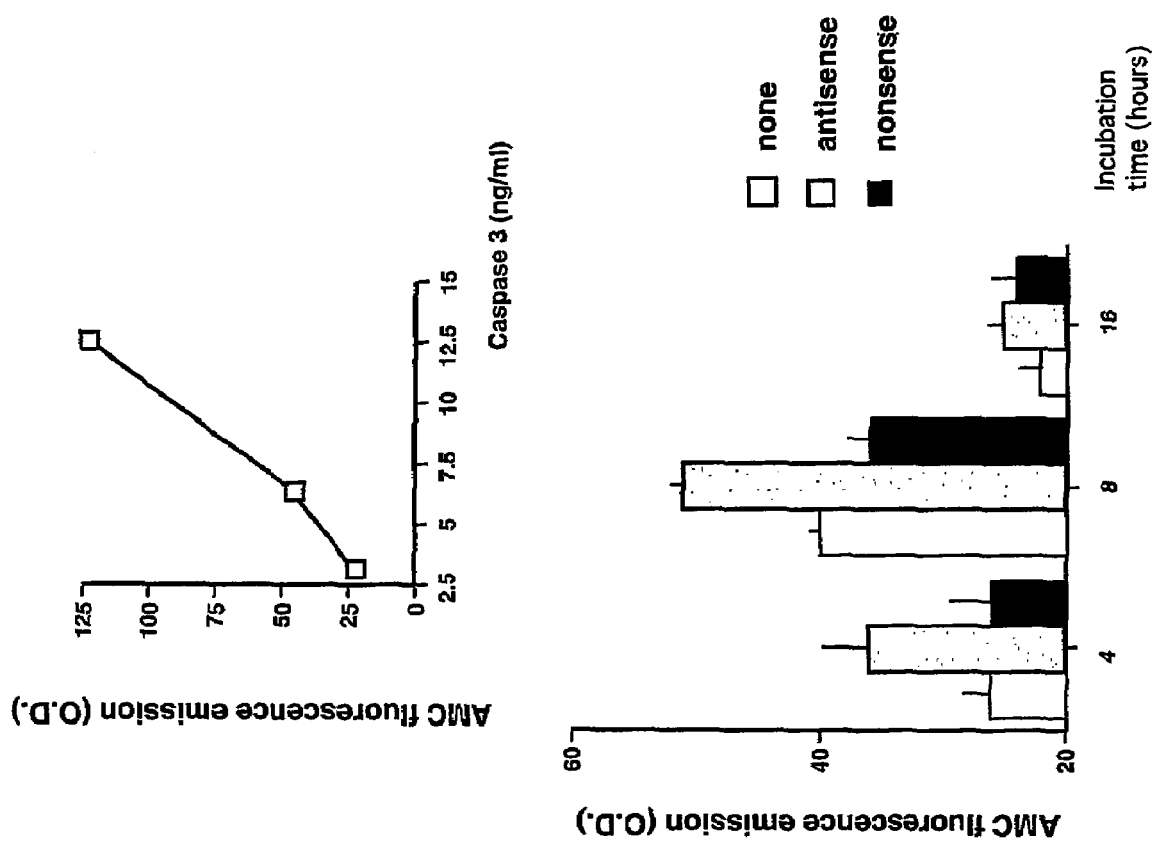
FIG. 4 shows the stimulation of caspase activity by anti-BAG3 antisense oligodeoxynucleotides in primary cells from leukemia patients.

FIG. 4—Effect of anti-BAG3 antisense oligodeoxynucleotides on caspase 3 activity in B-CLLs. Leukemic cells were isolated from B-CLL patients' peripheral blood specimens by centrifugation through Ficoll-Hypaque and cultured for the indicated times without or with the BAG3 antisense or control nonsense phosphorothioate oligodeoxynucleotides (5 microM) described in the text. Then cell extracts were obtained and caspase 3 activity was analysed according to ref. 9.

Figure 5:
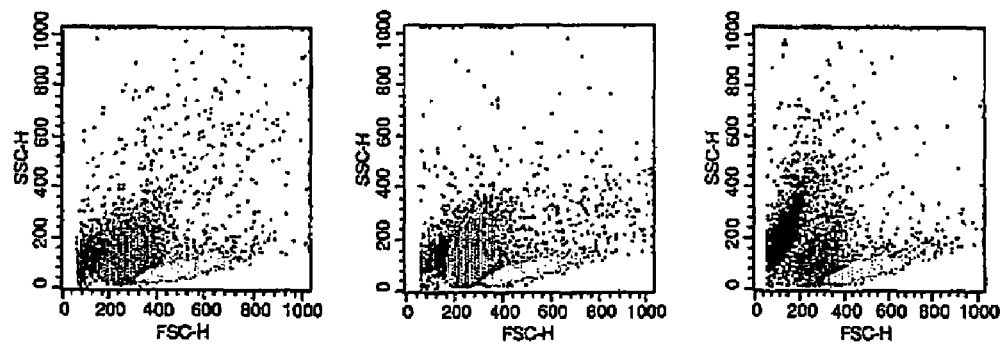
FIG. 5 shows the enhancement on annexin V binding by anti-BAG3 antisense oligodeoxynucleotides in primary cells from leukemia patients.
Figure 5:
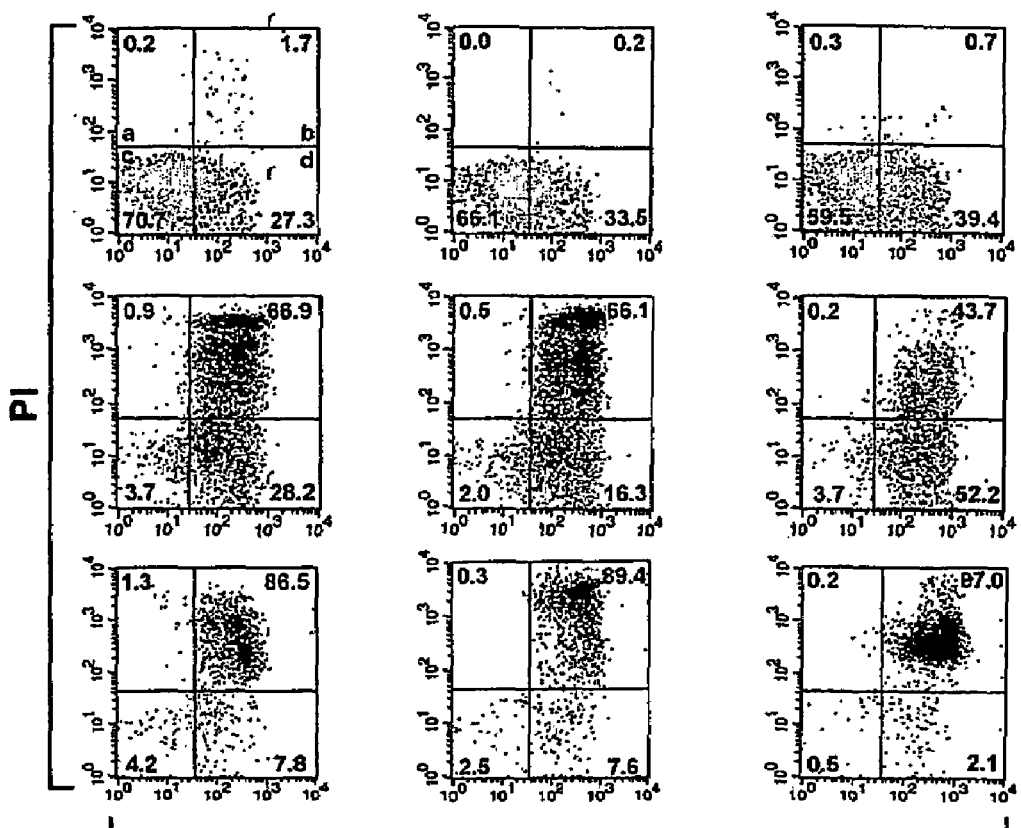

FIG. 5—Effect of anti-BAG3 antisense oligodeoxynucleotides on annexin V binding in B-CLLs Leukemic cells were isolated from B-CLL patients' peripheral blood specimens by centrifugation through Ficoll-Hypaque and cultured for 40 hours the indicated times without or with the BAG3 antisense or control nonsense phosphorothioate oligodeoxynucleotides (5 microM) described in the text. Then cell vitality was analysed by propidium iodide incorporation in non permeabilized cells, while at the same time annexin V binding was analysed by immunofluorescence according to ref. 10. A: percentages of alive, apoptotic and dead cells in the cytogram regions; B: PI-versus Annexin V-staining.

FIG. 6—Effect of anti-BAG3 antisense oligodeoxynucleotides on apoptosis in 15 B-CLL specimens Leukemic cells were isolated from B-CLL patients' peripheral blood specimens by centrifugation through Ficoll-Hypaque and cultured for 5 days without or with fludarabine phosphate (2 microgr/ml) and/or the BAG3 antisense or control nonsense phosphorothioate oligodeoxynucleotides (5 microM) described in the text. Then cell apoptosis was analysed by cell permeabilization and PI staining according to ref. 11.

FIG. 7—Effect of anti-BAG3 antisense oligodeoxynucleotides on ALL cell apoptosis Leukemic cells were isolated from ALL patients' peripheral blood specimens by centrifugation through Ficoll-Hypaque and cultured for four days (A panel) or the indicated times (B panel) without or with cytosine arabinoside (AraC, 1 microM) and/or the BAG3 antisense or control nonsense phosphorothioate oligodeoxynucleotides (5 microM) described in the text. Then cell apoptosis was analysed by cell permeabilization and PI staining according to ref. 11.

Table 1—Effect of anti-BAG3 antisense oligodeoxynucleotides on apoptosis in cells of the human osteosarcoma line SAOS.

TABLE 1

Effect of anti-BAG3 antisense oligodeoxynucleotides on apoptosis in cells of the human osteosarcoma line SAOS.

| | Incubation | | |
|---|---|---|---|
| Oligo | Control medium | Etoposide (5 microM) | Topotecan (40 ng/ml) |
| | 17.74* | 38.32 | 36.84 |
| BAG3 antisense | 52.38 | 73.40 | 68.62 |
| control nonsense | 25.84 | 45.40 | 41.60 |

*% of apoptosis

Cells of the SAOS line were incubated for 72 h in 10% FCS-RPMI without or with chemotherapeutic compounds (etoposide or topotecan) and/or the BAG3 antisense or control nonsense phosphorothioate oligodeoxynucleotides (5 microM) described in the text. Then cell apoptosis was analysed by cell permeabilization and PI staining according to ref.11.

Figure 8:
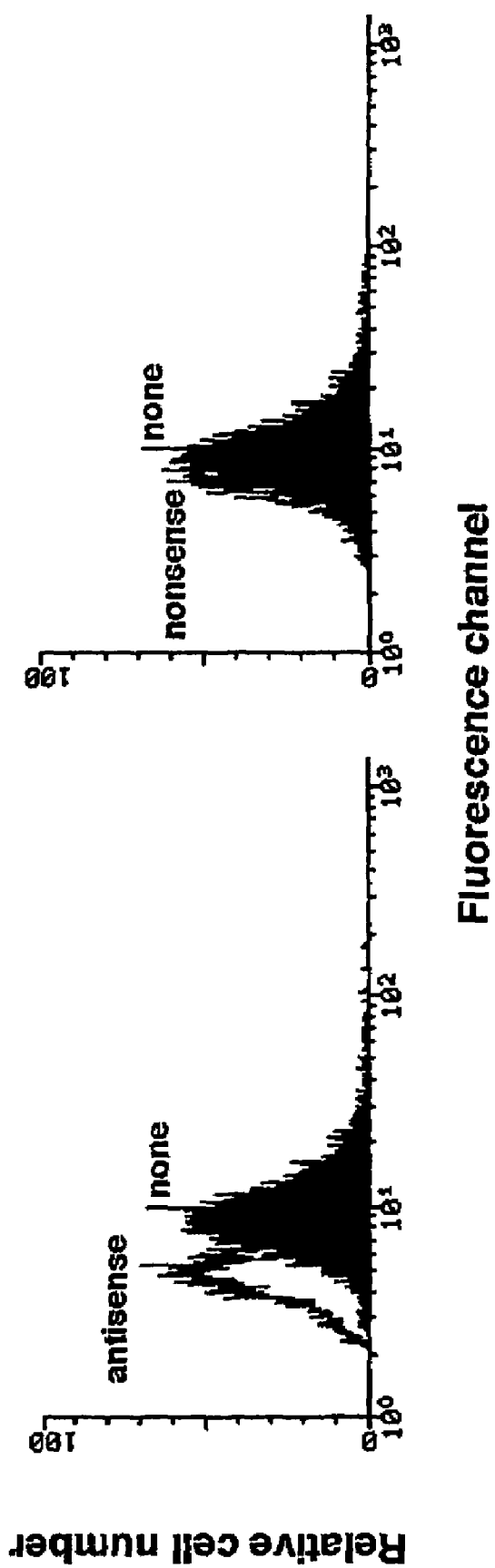
FIG. 8 shows the BAG3 downmodulation ability of anti-BAG3 antisense oligodeoxynucleotides in human U937 cells.

FIG. 8—Effect of anti-BAG3 antisense oligodeoxynucleotides on BAG3 protein levels in cells of the human myeloid leukemia line U937 U937 cells were cultured for 24 hours in 10% FCS-RPMI without or with the BAG3 antisense or control nonsense phosphorothioate oligodeoxynucleotides (5 microM) described in the text. Then cells were permeabilised and analysed by indirect immunofluorescence with AC-BAG3-1.

FIG. 9—Effect of anti-BAG3 antisense oligodeoxynucleotides on stress-induced apoptosis in cells of the human myeloid leukemia line U937 U937 cells were cultured for 40 h without or with diethylmaleate (DEM, 1.2 microM) and/or the BAG3 antisense or control nonsense phosphorothioate oligodeoxynucleotides (5 microM) described in the text. Then cell apoptosis was analysed by cell permeabilization and PI staining according to ref.11.

FIG. 10—Effect of anti-BAG3 antisense oligodeoxynucleotides on stress-induced apoptosis in normal human peripheral blood leucocytes Lymphocytes (A panel) and monocytes (B panel) were obtained from human normal peripheral blood specimens by centrifugation through a Ficoll-Hypaque 50-72% density gradient and cultured in 10% FCS-RPMI for 48 hours with or without a combination of DEM (1.2 microM) and 2ME (20 microM) and/or the or the BAG3 antisense or control nonsense phosphorothioate oligodeoxynucleotides (5 microM) described in the text. Then cell apoptosis was analysed by cell permeabilization and PI staining according to ref. 11.

TABLE 2

Protective effect of BAG3 hyperexpression on stress-induced apoptosis in the human cell line 293.

| Transfected construct | Incubation | % of apoptosis |
|---|---|---|
| Control pcDNA | control medium | 6.1 ± 0.3* |
| | DEM + 2ME | 32.4 ± 1.2 |
| BAG3-pcDNA | control medium | 5.3 ± 0.2 |
| | DEM + 2ME | 13.4 ± 0.5 |

*mean of duplicates ± SD

Cells of the human line 293 were transfected using a Fugene (Roche) preparation with a pcDNA construct hyperexpressing BAG3 or a void control pcDNA. BAG3 protein hyperexpression was verified by immunofluorescence. Then the cells were incubated for 48 hours in 10% FCS-RPMI with or without a combination of DEM+2ME and apoptosis was analysed by cell permeabilization and PI staining according to ref.11.

TABLE 3

BAG3 expression influences the growth of human neoplastic (osteosarcoma) cells xenografted in nude mice
Human osteosarcoma cells of the SaOs line ($10 \times 10^6$), wild type (A) or stably transfected with a BAG3- hyperexpressing (B) or a control void (C) vector, were injected in 6 week-old nu/nu mice; tumour volume was measured every week. Final results at the end of the 8th week are reported.

| # | mouse | tumour volume (mm$^3$) |
|---|---|---|
| | | <40 |
| | B | 65 |
| | C | <40 |
| 2 | A | <40 |
| | B | 45 |
| | C | <40 |
| 3 | A | <40 |
| | B | .92 |
| | C | <40 |
| 4 | A | <40 |
| | B | <40 |
| | C | <40 |
| 5 | A | <40 |
| | B | 65 |
| | C | <40 |

Figure 11:
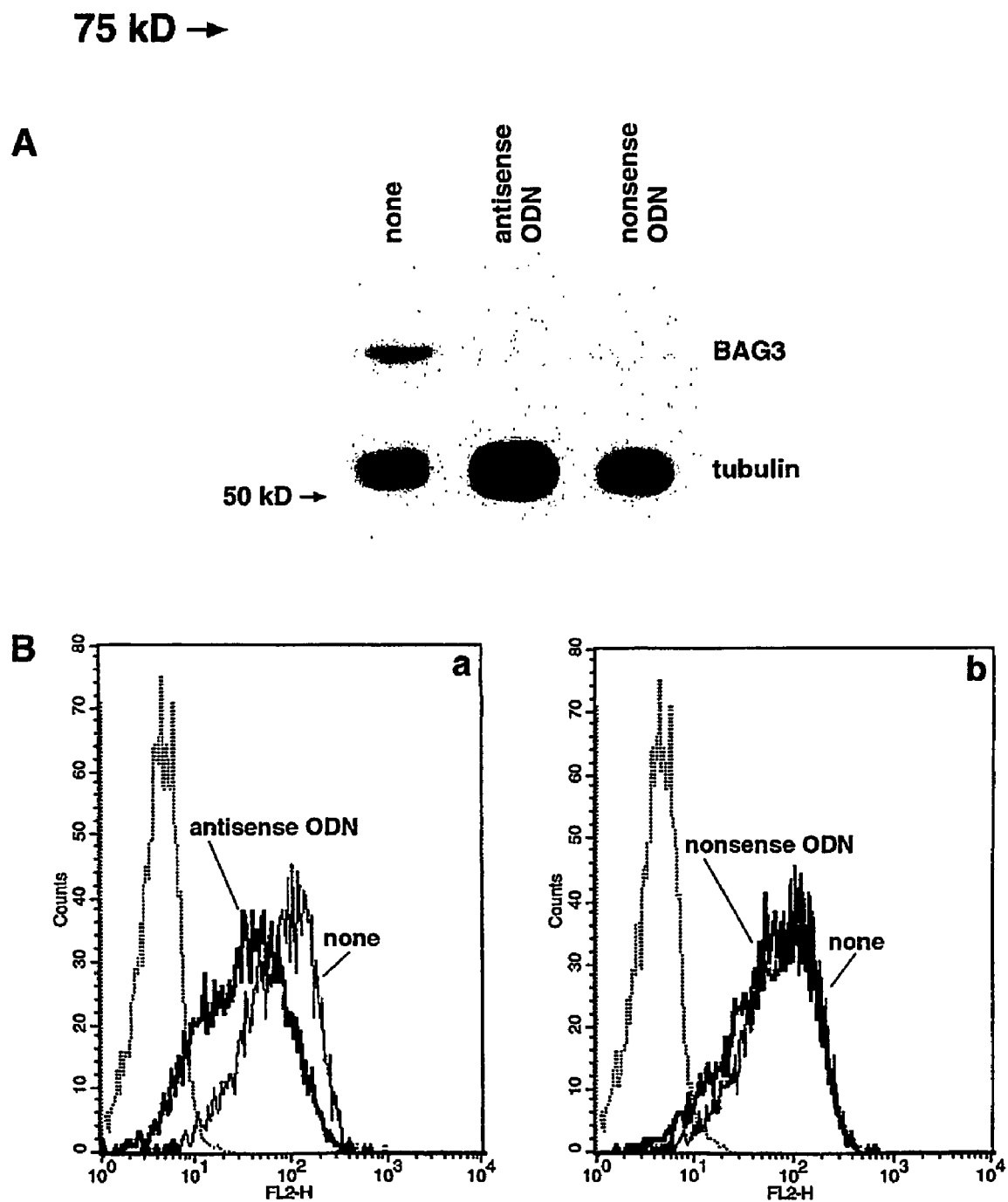
FIG. 11 shows the expression of BAG-3 protein and its modulation by antisense oligonucleotides, as detected in Western blotting (A) or intracellular immunofluorescence (B).

FIG. 11 Expression of BAG3 protein in ALL cells and its downmodulation by BAG3-specific antisense oligonucleotides. A—ALL cells ($1 \times 10^6$/ml) were cultured in 10% FCS-RPMI without or with control nonsense (TTATATTCTAT-TATATTTATGAACTCC, SEQ ID NO 12, nonsense 1) or BAG3-specific antisense (TGCATCATGGGC-GAGTGGGTGGCGG, SEQ ID NO 9, antisense 1) oligonucleotides (5 microM) for 24 hr. Then cell lysates were obtained and analyzed in Western blot with anti-BAG3 (AC-BAG3-1; analogous results were obtained With AC-BAG3-2) or anti-tubulin antibodies. B—ALL cells ($1 \times 10^6$/ml) were cultured in 10% FCS-RPMI without or with BAG3-specific antisense (TGCATCATGGGCGAGTGGGTGGCGG, SEQ ID NO 9, antisense 1) (a) or control nonsense (TTATATTC-TATTATATTTATGAACTCC, SEQ ID NO 12, nonsense 1) (b) oligonucleotides (5 microM) for 24 hr. Then the cells were analyzed by intracellular immunofluorescence with the anti-BAG3 polyclonal antibody. Negative controls with a control rabbit antibody preparation are shown on the left in a and b. Results are representative of experiments with at least three different ALL samples; comparable results were obtained using any one of the three antisense or nonsense ODN.

Figure 12:
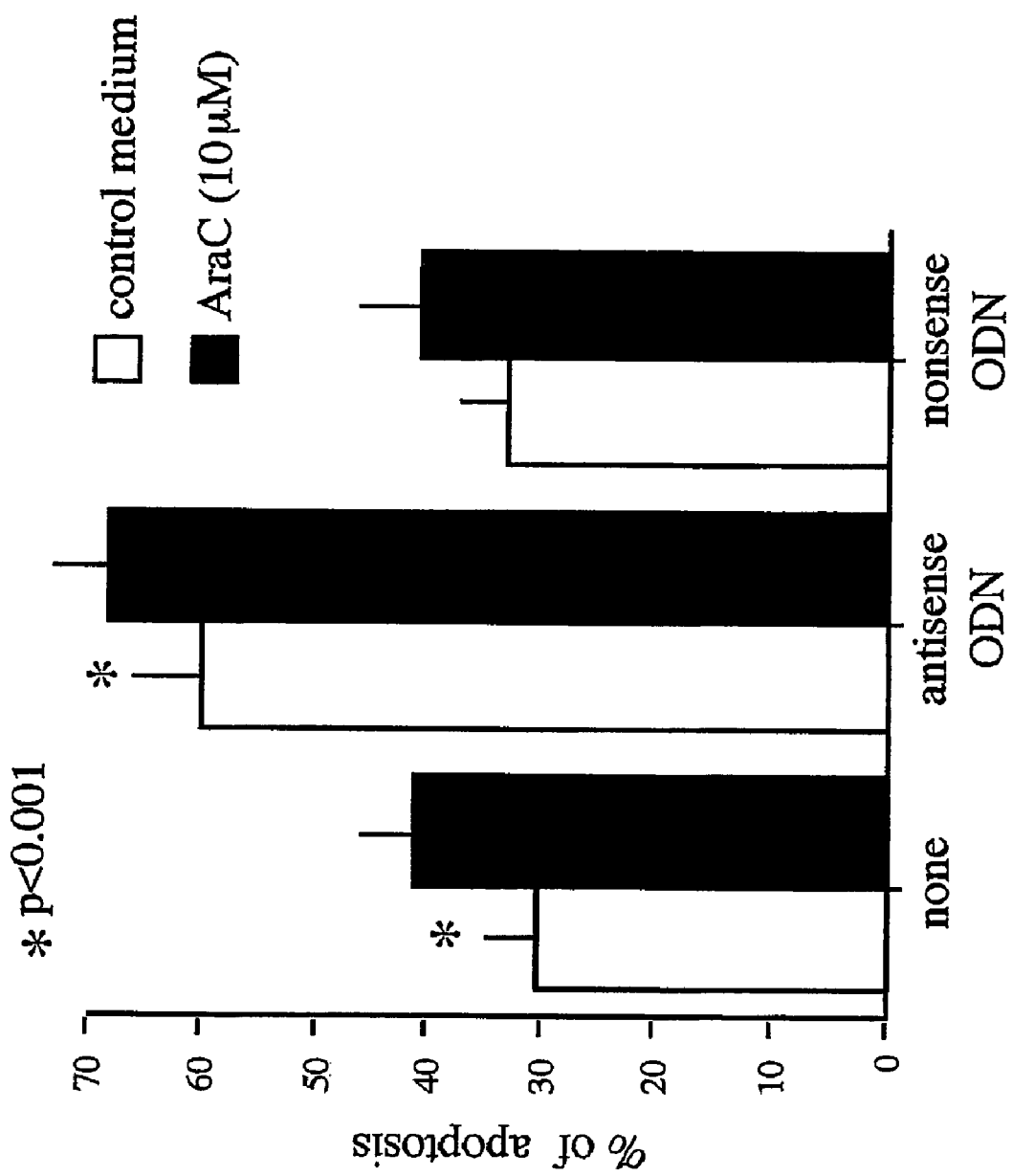
FIG. 12 shows the effect of BAG3-specific antisense oligonucleotides or AraC on ALL cell apoptosis.

FIG. 12—Effects of BAG3-specific antisense oligonucleotidesor AraC on ALL cell apoptosis. A—ALL cells ($1 \times 10^6$/ml) from ten different samples were cultured in 10% FCS-RPMI without or with control nonsense or BAG3-specific antisense oligonucleotides (5 microM), or with AraC (10 microM), for 4 days. Then cell apoptosis was analyzed by propidium iodide incorporation in permeabilized cells and flow cytometry. Student's t test was performed to evaluate the difference between apoptosis percentages detected in control and BAG3 antisense-cultured cells, respectively.

TABLE 4

Binding of hybridoma mother clone supernatants to MAP-BAG3 constructs as detecteds by ELISA test.
ELISA test of antibodies produced by the monoclonal mother clones, AC-1, AC-2, AC-3, AC-4, AC-5, AC-6, AC-7, AC-8, AC-9. Supernatants were obtained from nine hybridoma mother clones (AC-1 to -9) and analysed for their binding to MAP-BAG3 constructs.

|  | Map 1 | Map 2 | Map 3 | Map 4 | Map 1 | Map 2 | Map 3 | Map 4 | Map 1 | Map 2 | Map 3 | Map 4 |
|---|---|---|---|---|---|---|---|---|---|---|---|---|
| 1/2 | 1,254 | 2,475 | 0,050 | 0,042 | 1,808 | 0,504 | 0,412 | 0,424 | 3,825 | 0,054 | 0,053 | 0,050 |
| 1/10 | 0,345 | 0,966 | 0,047 | 0,042 | 0,474 | 0,137 | 0,128 | 0,123 | 3,756 | 0,053 | 0,050 | 0,046 |
| 1/2 | 2,012 | 1,568 | 0,047 | 0,042 | 1,782 | 0,666 | 0,438 | 0,451 | 3,747 | 0,059 | 0,065 | 0,062 |
| 1/10 | 0,715 | 0,460 | 0,045 | 0,042 | 0,608 | 0,164 | 0,150 | 0,149 | 3,729 | 0,046 | 0,051 | 0,049 |
| 1/2 | 0,044 | 0,048 | 0,300 | 0,046 | 2,133 | 0,646 | 0,547 | 0,396 | 3,822 | 0,047 | 0,047 | 0,052 |
| 1/10 | 0,042 | 0,046 | 0,109 | 0,045 | 0,580 | 0,154 | 0,140 | 0,138 | 3,556 | 0,049 | 0,046 | 0,048 |
| 1/2 |  | AC-4 |  |  |  | AC-1 |  |  |  | AC-7 |  |  |
| 1/10 |  |  |  |  |  |  |  |  |  |  |  |  |
| 1/2 |  | AC-5 |  |  |  | AC-2 |  |  |  | AC-8 |  |  |
| 1/10 |  |  |  |  |  |  |  |  |  |  |  |  |
| 1/2 |  | AC-6 |  |  |  | AC-3 |  |  |  | AC-9 |  |  |
| 1/10 |  |  |  |  |  |  |  |  |  |  |  |  |

FIG. 13 Binding of BAG3-specific polyclonal and monoclonal antibodies to proteins from HeLa or primary acute leukemia cells. A—Lysates from HeLa or primary acute leukemia cells were analysed in Western blotting using AC-BAG3-1 (central lanes: 3 and 4) or AC-BAG3-2 (lanes 1, 2 and 5) antibodies (A). B—Supernatants from the hybridoma mother clones AC-1 (1), AC-2 (2), AC-3 (3) or AC-4 (4) were analysed for their binding to proteins from HeLa cells in Western blotting.

REFERENCES

1. Nicholson D W. 2000. From bench to clinic with apoptosis-based therapeutic agents. Nature 407: 810.
2. Takayama S and Reed J C. 2001. Molecular chaperone targeting and regulation by BAG family proteins. Nature Cell Biology 3: E237.
3. Takayama T, Xie Z, and Reed J C. 1999. An evolutionarily conserved family of Hsp70/Hsc70 molecular chaperone regulators. J Biol Chem 274: 781.
4. Doong H, Price J, Kim Y-S, Gasbarre C, Probst J, Liotta L A, Blanchette J, Rizzo K, and Khon E. 2000. CAIR-1/BAG-3 forms and EGF-regulated ternary complex with phospholipase C gamma and Hsp70/Hsc70. Oncogene 19: 4385.
5. Lee J-H, Takahashi T, Yasuhara N, Inazawa J, Kamada S, Tsujimoto Y. 1999. Bis, a Bcl-2-binding protein that synergize with Bcl-2 in preventing cell death. Oncogene 18: 6183.
6. Liao O, Ozawa F, Friess H, Zimmermann A, Takayama S, Reed J C, Kleeff J, Buchler M W. 2001.The anti-apoptotic protein BAG-3 is overexpressed in pancreatic cancer and induced by heat stress in pancreatic cancer cell lines. FEBS Lett. 503:151.
7. Antoku K, Maser R S, Scully W J Jr, Delach S M, and Johnson D E. 2001. Isolation of Bcl-2 binding proteins that exhibit homology with BAG-1 and Suppressor of Death Domains protein. Biochem Biophys Res Comm 286: 1003.
8. Renz A, Berdel W E, Kreuter M, Belka C, Schulze-Osthoff K, Los M. 2001. Rapid extracellular release of cytochrome c is specific for apoptosis and marks cell death in vivo. Blood 98:1542.
9. Kluck R M, Martin S J, Hoffman B M, Zhou J S, Green D R and Newmeyer D D. 1997. Cytochrome c activation of CPP32-like proteolysis plays a critical role in a Xenopus cell-free apoptosis system. EMBO J. 16: 4639.
10. Koopman G, Reutelingsperger C P, Kuijten G A, Keehnen R M, Pals S T, van Oers M H. 1994. Annexin V for flow cytometric detection of phosphatidylserine expression on B cells undergoing apoptosis. Blood. 84:1415.
11. Nicoletti I, Migliorati G, Pagliacci M C, Grignani F, Riccardi C A. 1991. A rapid and simple method for measuring thymocyte apoptosis by propidium iodide staining and flow cytometry. J Immunol Methods 139: 271.
12. Tassone P, Tuccillo F, Bonelli P, Turco M C, Cecco L, Cerra M, Bond H M, Barbieri V, Venuta S. 1998. CD36 is rapidly and transiently upregulated on phytohemagglutinin (PHA)-stimulated peripheralblood lymphocytes. Analysis by a new monoclonal antibody (UN7).Tissue Antigens 51: 671.
13. Romano M F, Lamberti A, Tassone P, Alfinito F, Costantini S, Chiurazzi F, Defrance T, Bonelli P, Tuccillo F, Turco M C, Venuta S. 1998. Triggering of CD40 antigen inhibits fludarabine-induced apoptosis in B-CLL cells. Blood 92: 990.
14. Manolagas S C. 2001. Manipulating programmed cell death for better living. Sci STRKE 19: 87.
15. Drissi R, Zindy F, Roussel M F, Cleveland J L. c-Myc-mediated regulation of telomerase activity is disabled in immortalized cells. 2001. J Biol Chem 276: 29994.
16. Petit-Frere C, Capulas E, Lyon D A, Norbury C J, Lowe J E, Clingen P H, Riballo E, Green M H, Arlett C F. 2000. Apoptosis and cytokine release induced by ionizing or ultraviolet B radiation in primary and immortalized human keratinocytes. Carcinogenesis 21: 1087.
17. Brezden C B, Rauth A M. 1996. Differential cell death in immortalized and non-immortalized cells at confluency. Oncogene 12: 201.
18. Iordanov M S, Wong J, Newton D L, Rybak S M, Bright R K, Flavell R A, Davis R J, Magun B E. 2000. Differential requirement for the stress-activated protein kinase/c-Jun NH(2)-terminal kinase in RNAdamage-induced apoptosis in primary and in immortalized fibroblasts. Mol Cell Biol Res Commun 4:122.
19. Marsden V S, Strasser A. 2000. Control of Apoptosis in the Immune System: Bcl-2, BH3-Only Proteins and More. Annu Rev Immunol, Oct. 16, 2002.
20. :Roth W, Grimmel C, Rieger L, Strik H, Takayama S, Krajewski S, Meyermann R, Dichgans J, Reed J C, Weller M. 2000. Bag-1 and Bcl-2 gene transfer in malignant glioma: modulation of cell cycle regulation and apoptosis. Brain Pathol. 10: 223.
21. Zong W X, Lindsten T, Ross A J, MacGregor G R, Thompson C B. 2001. BH3-only proteins that bind pro-survival Bcl-2 family members fail to induce apoptosis in the absence of Bax and Bak. Genes Dev 15: 1481.
22. Gewirtz A M. 1999. Oligonucleotide therapeutics: clothing the emperor. Curr Opin Mol Ther 3: 297.
23. Opalinska J B, Gewirtz A M. 2002. Nucleic-acid therapeutics: basic principles and recent applications. Nat Rev Drug Discov 7: 503.
24. Keah H H, Kecorius E, Hearn M T. 1988. Direct synthesis and characterisation of multi-dendritic peptides for use as immunogens. J Pept Res 51: 2.
25. Tam J P. 1988. Synthetic peptide vaccine design: synthesis and properties of a high-density multiple antigenic peptide system. Proc Natl Acad Sci USA 85: 5409.
26. Ota S, Ono T, Morita A, Uenaka A, Harada M, Nakayama E. 2002. Cellular processing of a multibranched lysine core with tumor antigen peptides and presentation of peptide epitopes recognized by cytotoxic T lymphocytes on antigen-presenting cells. Cancer Res 62.:1471.

The invention claimed is:

1. A monoclonal antibody secreted by the hybridoma clone AC-1, deposit number PD02009.

2. The hybridoma clone AC-1, deposit number PD02009.

3. A peptide construct, said peptide construct being a Multiple Antigen Peptide (MAP) construct selected from the group of MAP constructs consisting of:

```
MAP-BAG3-1:
NH₂-DRDPLPPGWEIKIDPQ(SEQ ID NO: 15)-MAP;

MAP-BAG3-2:
NH₂-SSPKSVATEERAAPS(SEQ ID NO: 16)-MAP;

MAP-BAG3-3:
NH₂-DKGKKNAGNAEDPHT(SEQ ID NO: 17)-MAP;

MAP-BAG3-4:
NH₂-NPSSMTDTPGNPAAP(SEQ ID NO: 18)-MAP;
```

4. A composition comprising the monoclonal antibody of claim 1 and a pharmaceutically acceptable carrier.

5. A kit for identification and diagnosis of a disease characterized by regulation of BAG3 protein expression, said kit comprising one or more containers, wherein at least one containing the monoclonal antibody according to claim 1.

* * * * *

SEQUENCE LISTING

```
<160> NUMBER OF SEQ ID NOS: 18

<210> SEQ ID NO 1
<211> LENGTH: 2533
<212> TYPE: DNA
<213> ORGANISM: Homo sapiens
<220> FEATURE:
<221> NAME/KEY: CDS
<222> LOCATION: (307)..(2034)
<223> OTHER INFORMATION: Human BAG3 gene sequence
      NCBI Pub Med  Accession Number: XM_055575
      Homo sapiens BCL2-associated athanogene 3 (BAG3)

<400> SEQUENCE: 1
gcggagctcc gcatccaacc ccgggccgcg gccaacttt ttggactgga ccagaagttt      60
ctagccggcc agttgctacc tcccttatc tcctccttcc cctctggcag cgaggaggct    120
atttccagac acttccaccc ctctctggcc acgtcacccc cgcctttaat tcataaaggt    180
gcccggcgcc ggcttcccgg acacgtcggc ggcggagagg ggcccacggc ggcggcccgg    240
ccagagactc ggcgcccgga gccagcgccc cgcacccgcg cccagcgggg cagaccccaa    300 cccagc atg agc gcc gcc acc cac tcg ccc atg atg cag gtg gcg tcc      348
       Met Ser Ala Ala Thr His Ser Pro Met Met Gln Val Ala Ser
       1               5                  10 ggc aac ggt gac cgc gac cct ttg ccc ccc gga tgg gag atc aag atc      396
Gly Asn Gly Asp Arg Asp Pro Leu Pro Pro Gly Trp Glu Ile Lys Ile
15                  20                  25                  30 gac ccg cag acc ggc tgg ccc ttc ttc gtg gac cac aac agc cgc acc      444
Asp Pro Gln Thr Gly Trp Pro Phe Phe Val Asp His Asn Ser Arg Thr
                35                  40                  45 act acg tgg aac gac ccg cgc gtg ccc tct gag ggc ccc aag gag act      492
Thr Thr Trp Asn Asp Pro Arg Val Pro Ser Glu Gly Pro Lys Glu Thr
            50                  55                  60 cca tcc tct gcc aat ggc cct tcc cgg gag ggc tct agg ctg ccg cct      540
Pro Ser Ser Ala Asn Gly Pro Ser Arg Glu Gly Ser Arg Leu Pro Pro
        65                  70                  75 gct agg gaa ggc cac cct gtg tac ccc cag ctc cga cca ggc tac att      588
Ala Arg Glu Gly His Pro Val Tyr Pro Gln Leu Arg Pro Gly Tyr Ile
    80                  85                  90 ccc att cct gtg ctc cat gaa ggc gct gag aac cgg cag gtg cac cct      636
Pro Ile Pro Val Leu His Glu Gly Ala Glu Asn Arg Gln Val His Pro
95                  100                 105                 110 ttc cat gtc tat ccc cag cct ggg atg cag cga ttc cga act gag gcg      684
Phe His Val Tyr Pro Gln Pro Gly Met Gln Arg Phe Arg Thr Glu Ala
                115                 120                 125 gca gca gcg gct cct cag agg tcc cag tca cct ctg cgg ggc atg cca      732
Ala Ala Ala Ala Pro Gln Arg Ser Gln Ser Pro Leu Arg Gly Met Pro
            130                 135                 140
```

```
                                                      -continued gaa acc act cag cca gat aaa cag tgt gga cag gtg gca gcg gcg gcg        780
Glu Thr Thr Gln Pro Asp Lys Gln Cys Gly Gln Val Ala Ala Ala Ala
        145                 150                 155 gca gcc cag ccc cca gcc tcc cac gga cct gag cgg tcc cag tct cca        828
Ala Ala Gln Pro Pro Ala Ser His Gly Pro Glu Arg Ser Gln Ser Pro
    160                 165                 170 gct gcc tct gac tgc tca tcc tca tcc tcg gcc agc ctg cct tcc            876
Ala Ala Ser Asp Cys Ser Ser Ser Ser Ser Ala Ser Leu Pro Ser
175                 180                 185                 190 tcc ggc agg agc agc ctg ggc agt cac cag ctc ccg ggg tac atc            924
Ser Gly Arg Ser Ser Leu Gly Ser His Gln Leu Pro Arg Gly Tyr Ile
                195                 200                 205 tcc att ccg gtg ata cac gag cag aac gtt acc cgg cca gca gcc cag        972
Ser Ile Pro Val Ile His Glu Gln Asn Val Thr Arg Pro Ala Ala Gln
        210                 215                 220 ccc tcc ttc cac caa gcc cag aag acg cac tac cca gcg cag cag ggg       1020
Pro Ser Phe His Gln Ala Gln Lys Thr His Tyr Pro Ala Gln Gln Gly
    225                 230                 235 gag tac cag acc cac cag cct gtg tac cac aag atc cag ggg gat gac       1068
Glu Tyr Gln Thr His Gln Pro Val Tyr His Lys Ile Gln Gly Asp Asp
240                 245                 250 tgg gag ccc cgg ccc ctg cgg gcg gca tcc ccg ttc agg tca tct gtc       1116
Trp Glu Pro Arg Pro Leu Arg Ala Ala Ser Pro Phe Arg Ser Ser Val
255                 260                 265                 270 cag ggt gca tcg agc cgg gag ggc tca cca gcc agg agc agc acg cca       1164
Gln Gly Ala Ser Ser Arg Glu Gly Ser Pro Ala Arg Ser Ser Thr Pro
                275                 280                 285 ctc cac tcc ccc tcg ccc atc cgt gtg cac acc gtg gtc gac agg cct       1212
Leu His Ser Pro Ser Pro Ile Arg Val His Thr Val Val Asp Arg Pro
        290                 295                 300 cag cag ccc atg acc cat cga gaa act gca cct gtt tcc cag cct gaa       1260
Gln Gln Pro Met Thr His Arg Glu Thr Ala Pro Val Ser Gln Pro Glu
    305                 310                 315 aac aaa cca gaa agt aag cca ggc cca gtt gga cca gaa ctc cct cct       1308
Asn Lys Pro Glu Ser Lys Pro Gly Pro Val Gly Pro Glu Leu Pro Pro
320                 325                 330 gga cac atc cca att caa gtg atc cgc aaa gag gtg gat tct aaa cct       1356
Gly His Ile Pro Ile Gln Val Ile Arg Lys Glu Val Asp Ser Lys Pro
335                 340                 345                 350 gtt tcc cag aag ccc cca cct ccc tct gag aag gta gag gtg aaa gtt       1404
Val Ser Gln Lys Pro Pro Pro Pro Ser Glu Lys Val Glu Val Lys Val
                355                 360                 365 ccc cct gct cca gtt cct tgt cct cct ccc agc cct ggc cct tct gct       1452
Pro Pro Ala Pro Val Pro Cys Pro Pro Pro Ser Pro Gly Pro Ser Ala
        370                 375                 380 gtc ccc tct tcc ccc aag agt gtg gct aca gaa gag agg gca gcc ccc       1500
Val Pro Ser Ser Pro Lys Ser Val Ala Thr Glu Glu Arg Ala Ala Pro
    385                 390                 395 agc act gcc cct gca gaa gct aca cct cca aaa cca gga gaa gcc gag       1548
Ser Thr Ala Pro Ala Glu Ala Thr Pro Pro Lys Pro Gly Glu Ala Glu
400                 405                 410 gct ccc cca aaa cat cca gga gtg ctg aaa gtg gaa gcc atc ctg gag       1596
Ala Pro Pro Lys His Pro Gly Val Leu Lys Val Glu Ala Ile Leu Glu
415                 420                 425                 430 aag gtg cag ggg ctg gag cag gct gta gac aac ttt gaa ggc aag aag       1644
Lys Val Gln Gly Leu Glu Gln Ala Val Asp Asn Phe Glu Gly Lys Lys
                435                 440                 445 act gac aaa aag tac ctg atg atc gaa gag tat ttg acc aaa gag ctg       1692
Thr Asp Lys Lys Tyr Leu Met Ile Glu Glu Tyr Leu Thr Lys Glu Leu
```

```
            450                 455                 460
ctg gcc ctg gat tca gtg gac ccc gag gga cga gcc gat gtg cgt cag    1740
Leu Ala Leu Asp Ser Val Asp Pro Glu Gly Arg Ala Asp Val Arg Gln
            465                 470                 475 gcc agg aga gac ggt gtc agg aag gtt cag acc atc ttg gaa aaa ctt    1788
Ala Arg Arg Asp Gly Val Arg Lys Val Gln Thr Ile Leu Glu Lys Leu
        480                 485                 490 gaa cag aaa gcc att gat gtc cca ggt caa gtc cag gtc tat gaa ctc    1836
Glu Gln Lys Ala Ile Asp Val Pro Gly Gln Val Gln Val Tyr Glu Leu
495                 500                 505                 510 cag ccc agc aac ctt gaa gca gat cag cca ctg cag gca atc atg gag    1884
Gln Pro Ser Asn Leu Glu Ala Asp Gln Pro Leu Gln Ala Ile Met Glu
                515                 520                 525 atg ggt gcc gtg gca gca gac aag ggc aag aaa aat gct gga aat gca    1932
Met Gly Ala Val Ala Ala Asp Lys Gly Lys Lys Asn Ala Gly Asn Ala
                530                 535                 540 gaa gat ccc cac aca gaa acc cag cag cca gaa gcc aca gca gca gcg    1980
Glu Asp Pro His Thr Glu Thr Gln Gln Pro Glu Ala Thr Ala Ala Ala
            545                 550                 555 act tca aac ccc agc agc atg aca gac acc cct ggt aac cca gca gca    2028
Thr Ser Asn Pro Ser Ser Met Thr Asp Thr Pro Gly Asn Pro Ala Ala
        560                 565                 570 ccg tag cctctgccct gtaaaaatca gactcggaac cgatgtgtgc tttagggaat    2084
Pro
575 tttaagttgc atgcatttca gagactttaa gtcagttggt ttttattagc tgcttggtat    2144 gcagtaactt gggtggaggc aaaacactaa taaagggct aaaaggaaa atgatgcttt    2204 tcttctatat tcttactctg tacaaataaa gaagttgctt gttgtttcag aagtttaacc    2264 ccgttgcttg ttctgcagcc ctgtctactt gggcacccc accacctgtt agctgtggtt    2324 gtgcactgtc ttttgtagct ctggactgga ggggtagatg gggagtcaat tacccatcac    2384 ataaatatga acatttatc agaaatgttg ccattttaat gagatgattt tcttcatctc    2444 ataattaaaa tacctgactt tagagagagt aaaatgtgcc aggagccata ggaatatctg    2504 tatgttggat gactttaatg ctacatttt    2533

<210> SEQ ID NO 2
<211> LENGTH: 575
<212> TYPE: PRT
<213> ORGANISM: Homo sapiens

<400> SEQUENCE: 2

Met Ser Ala Ala Thr His Ser Pro Met Met Gln Val Ala Ser Gly Asn
1               5                   10                  15

Gly Asp Arg Asp Pro Leu Pro Pro Gly Trp Glu Ile Lys Ile Asp Pro
            20                  25                  30

Gln Thr Gly Trp Pro Phe Phe Val Asp His Asn Ser Arg Thr Thr Thr
        35                  40                  45

Trp Asn Asp Pro Arg Val Pro Ser Glu Gly Pro Lys Glu Thr Pro Ser
    50                  55                  60

Ser Ala Asn Gly Pro Ser Arg Glu Gly Ser Arg Leu Pro Pro Ala Arg
65                  70                  75                  80

Glu Gly His Pro Val Tyr Pro Gln Leu Arg Pro Gly Tyr Ile Pro Ile
                85                  90                  95

Pro Val Leu His Glu Gly Ala Glu Asn Arg Gln Val His Pro Phe His
            100                 105                 110
```

```
Val Tyr Pro Gln Pro Gly Met Gln Arg Phe Arg Thr Glu Ala Ala Ala
        115                 120                 125

Ala Ala Pro Gln Arg Ser Gln Ser Pro Leu Arg Gly Met Pro Glu Thr
        130                 135                 140

Thr Gln Pro Asp Lys Gln Cys Gly Gln Val Ala Ala Ala Ala Ala Ala
145                 150                 155                 160

Gln Pro Pro Ala Ser His Gly Pro Glu Arg Ser Gln Ser Pro Ala Ala
                165                 170                 175

Ser Asp Cys Ser Ser Ser Ser Ser Ala Ser Leu Pro Ser Ser Gly
            180                 185                 190

Arg Ser Ser Leu Gly Ser His Gln Leu Pro Arg Gly Tyr Ile Ser Ile
        195                 200                 205

Pro Val Ile His Glu Gln Asn Val Thr Arg Pro Ala Ala Gln Pro Ser
        210                 215                 220

Phe His Gln Ala Gln Lys Thr His Tyr Pro Ala Gln Gln Gly Glu Tyr
225                 230                 235                 240

Gln Thr His Gln Pro Val Tyr His Lys Ile Gln Gly Asp Asp Trp Glu
                245                 250                 255

Pro Arg Pro Leu Arg Ala Ala Ser Pro Phe Arg Ser Ser Val Gln Gly
            260                 265                 270

Ala Ser Ser Arg Glu Gly Ser Pro Ala Arg Ser Ser Thr Pro Leu His
        275                 280                 285

Ser Pro Ser Pro Ile Arg Val His Thr Val Val Asp Arg Pro Gln Gln
        290                 295                 300

Pro Met Thr His Arg Glu Thr Ala Pro Val Ser Gln Pro Glu Asn Lys
305                 310                 315                 320

Pro Glu Ser Lys Pro Gly Pro Val Gly Pro Glu Leu Pro Pro Gly His
                325                 330                 335

Ile Pro Ile Gln Val Ile Arg Lys Glu Val Asp Ser Lys Pro Val Ser
            340                 345                 350

Gln Lys Pro Pro Pro Ser Glu Lys Val Glu Val Lys Val Pro Pro Pro
        355                 360                 365

Ala Pro Val Pro Cys Pro Pro Ser Pro Gly Pro Ser Ala Val Pro
        370                 375                 380

Ser Ser Pro Lys Ser Val Ala Thr Glu Glu Arg Ala Ala Pro Ser Thr
385                 390                 395                 400

Ala Pro Ala Glu Ala Thr Pro Pro Lys Pro Gly Glu Ala Glu Ala Pro
                405                 410                 415

Pro Lys His Pro Gly Val Leu Lys Val Glu Ala Ile Leu Glu Lys Val
            420                 425                 430

Gln Gly Leu Glu Gln Ala Val Asp Asn Phe Glu Gly Lys Lys Thr Asp
        435                 440                 445

Lys Lys Tyr Leu Met Ile Glu Glu Tyr Leu Thr Lys Glu Leu Leu Ala
        450                 455                 460

Leu Asp Ser Val Asp Pro Glu Gly Arg Ala Asp Val Arg Gln Ala Arg
465                 470                 475                 480

Arg Asp Gly Val Arg Lys Val Gln Thr Ile Leu Glu Lys Leu Glu Gln
                485                 490                 495

Lys Ala Ile Asp Val Pro Gly Gln Val Gln Val Tyr Glu Leu Gln Pro
            500                 505                 510

Ser Asn Leu Glu Ala Asp Gln Pro Leu Gln Ala Ile Met Glu Met Gly
        515                 520                 525

Ala Val Ala Ala Asp Lys Gly Lys Lys Asn Ala Gly Asn Ala Glu Asp
```

```
                530             535             540
Pro His Thr Glu Thr Gln Gln Pro Glu Ala Thr Ala Ala Ala Thr Ser
545                 550                 555                 560

Asn Pro Ser Ser Met Thr Asp Thr Pro Gly Asn Pro Ala Ala Pro
                565                 570                 575
```

```
<210> SEQ ID NO 3
<211> LENGTH: 360
<212> TYPE: DNA
<213> ORGANISM: Homo sapiens
<220> FEATURE:
<221> NAME/KEY: misc_feature
<222> LOCATION: (1)..(360)
<223> OTHER INFORMATION: Specific sequence comprised inside BAG3 gene
      sequence

<400> SEQUENCE: 3
gcggagctcc gcatccaacc ccgggccgcg gccaacttttt ttggactgga ccagaagttt      60
ctagccggcc agttgctacc tcctttatc tcctccttcc cctctggcag cgaggaggct     120
atttccagac acttccaccc ctctctggca cgtcaccccc cgccttttaat tcataaaggt     180 gcccggcgcc ggcttccgg acacgtcggc ggcggagagg ggcccacggc ggcggcccgg     240
ccagagactc ggcgcccgga gccagcgccc cgcacccgcg ccccagcggg cagacccccaa     300 cccagcatga gcgccgccac ccactcgccc atgatgcagg tggcgtccgg caacggtgac     360
```

```
<210> SEQ ID NO 4
<211> LENGTH: 35
<212> TYPE: PRT
<213> ORGANISM: Homo sapiens
<220> FEATURE:
<221> NAME/KEY: PEPTIDE
<222> LOCATION: (1)..(35)
<223> OTHER INFORMATION: Specific sequence comprised inside BAG3 protein

<400> SEQUENCE: 4

Met Ser Ala Ala Thr His Ser Pro Met Met Gln Val Ala Ser Gly Asn
1               5                   10                  15

Gly Asp Arg Asp Pro Leu Pro Pro Gly Trp Glu Ile Lys Ile Asp Pro
                20                  25                  30

Gln Thr Gly
        35
```

```
<210> SEQ ID NO 5
<211> LENGTH: 1105
<212> TYPE: DNA
<213> ORGANISM: Homo sapiens
<220> FEATURE:
<221> NAME/KEY: misc_feature
<222> LOCATION: (1)..(1105)
<223> OTHER INFORMATION: Specific sequence comprised inside BAG3 gene
      sequence

<400> SEQUENCE: 5
gtgccctctg agggccccaa ggagactcca tcctctgcca atggcccttc ccgggagggc      60
tctaggctgc cgcctgctag ggaaggccac cctgtgtacc cccagctccg accaggctac     120
attcccattc ctgtgctcca tgaaggcgct gagaaccggc aggtgcaccc tttccatgtc     180 tatcccagc ctgggatgca gcgattccga actgaggcgg cagcagcggc tcctcagagg     240
tcccagtcac ctctgcgggg catgccagaa accactcagc cagataaaca gtgtggacag     300
gtggcagcgg cggcggcagc ccagccccca gcctcccacg gacctgagcg gtcccagtct     360
```

```
ccagctgcct ctgactgctc atcctcatcc tcctcggcca gcctgccttc ctccggcagg    420
agcagcctgg gcagtcacca gctcccgcgg gggtacatct ccattccggt gatacacgag    480
cagaacgtta cccggccagc agcccagccc tccttccacc aagcccagaa gacgcactac    540
ccagcgcagc agggggagta ccagacccac cagcctgtgt accacaagat ccaggggat    600 gactgggagc cccggcccct gcgggcggca tccccgttca ggtcatctgt ccagggtgca    660
tcgagccggg agggctcacc agccaggagc agcacgccac tccactcccc ctcgcccatc    720
cgtgtgcaca ccgtggtcga caggcctcag cagcccatga cccatcgaga aactgcacct    780
gtttcccagc ctgaaaacaa accagaaagt aagccaggcc cagttggacc agaactccct    840
cctggacaca tcccaattca agtgatccgc aaagaggtgg attctaaacc tgtttcccag    900
aagcccccac ctccctctga gaaggtagag gtgaaagttc ccctgctcc agttccttgt    960 cctcctccca gccctggccc ttctgctgtc ccctcttccc ccaagagtgt ggctacagaa   1020
gagagggcag ccccccagcac tgcccctgca gaagctacac tccaaaaacc aggagaagcc   1080
gaggctcccc caaaacatcc aggag                                          1105
```

<210> SEQ ID NO 6
<211> LENGTH: 395
<212> TYPE: PRT
<213> ORGANISM: Homo sapiens
<220> FEATURE:
<221> NAME/KEY: PEPTIDE
<222> LOCATION: (1)..(395)
<223> OTHER INFORMATION: Specific sequence comprised inside BAG3 protein

<400> SEQUENCE: 6

```
Asn Asp Pro Arg Val Pro Ser Glu Gly Pro Lys Glu Thr Pro Ser Ser
1               5                   10                  15

Ala Asn Gly Pro Ser Arg Glu Gly Ser Arg Leu Pro Pro Ala Arg Glu
            20                  25                  30

Gly His Pro Val Tyr Pro Gln Leu Arg Pro Gly Tyr Ile Pro Ile Pro
        35                  40                  45

Val Leu His Glu Gly Ala Glu Asn Arg Gln Val His Pro Phe His Val
    50                  55                  60

Tyr Pro Gln Pro Gly Met Gln Arg Phe Arg Thr Glu Ala Ala Ala Ala
65                  70                  75                  80

Ala Pro Gln Arg Ser Gln Ser Pro Leu Arg Gly Met Pro Glu Thr Thr
                85                  90                  95

Gln Pro Asp Lys Gln Cys Gly Gln Val Ala Ala Ala Ala Ala Ala Gln
            100                 105                 110

Pro Pro Ala Ser His Gly Pro Glu Arg Ser Gln Ser Pro Ala Ala Ser
        115                 120                 125

Asp Cys Ser Ser Ser Ser Ser Ala Ser Leu Pro Ser Ser Gly Arg
    130                 135                 140

Ser Ser Leu Gly Ser His Gln Leu Pro Arg Gly Tyr Ile Ser Ile Pro
145                 150                 155                 160

Val Ile His Glu Gln Asn Val Thr Arg Pro Ala Ala Gln Pro Ser Phe
                165                 170                 175

His Gln Ala Gln Lys Thr His Tyr Pro Ala Gln Gln Gly Glu Tyr Gln
            180                 185                 190

Thr His Gln Pro Val Tyr His Lys Ile Gln Gly Asp Asp Trp Glu Pro
        195                 200                 205

Arg Pro Leu Arg Ala Ala Ser Pro Phe Arg Ser Ser Val Gln Gly Ala
    210                 215                 220
```

Ser Ser Arg Glu Gly Ser Pro Ala Arg Ser Ser Thr Pro Leu His Ser
225                 230                 235                 240

Pro Ser Pro Ile Arg Val His Thr Val Val Asp Arg Pro Gln Gln Pro
            245                 250                 255

Met Thr His Arg Glu Thr Ala Pro Val Ser Gln Pro Glu Asn Lys Pro
            260                 265                 270

Glu Ser Lys Pro Gly Pro Val Gly Pro Glu Leu Pro Pro Gly His Ile
            275                 280                 285

Pro Ile Gln Val Ile Arg Lys Glu Val Asp Ser Lys Pro Val Ser Gln
            290                 295                 300

Lys Pro Pro Pro Ser Glu Lys Val Glu Val Lys Val Pro Pro Ala
305                 310                 315                 320

Pro Val Pro Cys Pro Pro Ser Pro Gly Pro Ser Ala Val Pro Ser
            325                 330                 335

Ser Pro Lys Ser Val Ala Thr Glu Glu Arg Ala Ala Pro Ser Thr Ala
            340                 345                 350

Pro Ala Glu Ala Thr Pro Pro Lys Pro Gly Glu Ala Glu Ala Pro Pro
            355                 360                 365

Lys His Pro Gly Val Leu Lys Val Glu Ala Ile Leu Glu Lys Val Gln
            370                 375                 380

Gly Leu Glu Gln Ala Val Asp Asn Phe Glu Gly
385                 390                 395

<210> SEQ ID NO 7
<211> LENGTH: 733
<212> TYPE: DNA
<213> ORGANISM: Homo sapiens
<220> FEATURE:
<221> NAME/KEY: misc_feature
<222> LOCATION: (1)..(733)
<223> OTHER INFORMATION: Specific sequence comprised inside BAG3 gene
      sequence

<400> SEQUENCE: 7
attgatgtcc caggtcaagt ccaggtctat gaactccagc ccagcaacct tgaagcagat        60
cagccactgc aggcaatcat ggagatgggt gccgtggcag cagacaaggg caagaaaaat       120
gctggaaatg cagaagatcc ccacacagaa acccagcagc cagaagccac agcagcagcg       180
acttcaaacc ccagcagcat gacagacacc cctggtaacc cagcagcacc gtagcctctg       240
ccctgtaaaa atcagactcg gaaccgatgt gtgctttagg gaattttaag ttgcatgcat       300
ttcagagact ttaagtcagt tggttttat tagctgcttg gtatgcagta acttgggtgg        360
aggcaaaaca ctaataaaag ggctaaaaag gaaaatgatg cttttcttct atattcttac       420
tctgtacaaa taagaagtt gcttgttgtt tcagaagttt aaccccgttg cttgttctgc       480
agccctgtct acttgggcac ccccaccacc tgttagctgt ggttgtgcac tgtcttttgt      540
agctctggac tggaggggta gatggggagt caattaccca tcacataaat atgaaacatt       600
tatcagaaat gttgccattt taatgagatg attttcttca tctcataatt aaaatacctg      660
actttagaga gagtaaaatg tgccaggagc cataggaata tctgtatgtt ggatgacttt       720
aatgctacat ttt                                                          733

<210> SEQ ID NO 8
<211> LENGTH: 67
<212> TYPE: PRT
<213> ORGANISM: Homo sapiens
<220> FEATURE:

```
<221> NAME/KEY: PEPTIDE
<222> LOCATION: (1)..(67)
<223> OTHER INFORMATION: Specific sequence comprised inside BAG3 protein

<400> SEQUENCE: 8

Glu Leu Gln Pro Ser Asn Leu Glu Ala Asp Gln Pro Leu Gln Ala Ile
1               5                   10                  15

Met Glu Met Gly Ala Val Ala Ala Asp Lys Gly Lys Lys Asn Ala Gly
            20                  25                  30

Asn Ala Glu Asp Pro His Thr Glu Thr Gln Gln Pro Glu Ala Thr Ala
        35                  40                  45

Ala Ala Thr Ser Asn Pro Ser Ser Met Thr Asp Thr Pro Gly Asn Pro
    50                  55                  60

Ala Ala Pro
65

<210> SEQ ID NO 9
<211> LENGTH: 25
<212> TYPE: DNA
<213> ORGANISM: Homo sapiens
<220> FEATURE:
<221> NAME/KEY: misc_feature
<222> LOCATION: (1)..(25)
<223> OTHER INFORMATION: BAG3-based specific antisense oligonucleotide

<400> SEQUENCE: 9
tgcatcatgg gcgagtgggt ggcgg                                         25

<210> SEQ ID NO 10
<211> LENGTH: 22
<212> TYPE: DNA
<213> ORGANISM: Homo sapiens
<220> FEATURE:
<221> NAME/KEY: misc_feature
<222> LOCATION: (1)..(22)
<223> OTHER INFORMATION: BAG3-based specific antisense oligonucleotide

<400> SEQUENCE: 10
gctcatgctg ggttggggtc tg                                            22

<210> SEQ ID NO 11
<211> LENGTH: 22
<212> TYPE: DNA
<213> ORGANISM: Homo sapiens
<220> FEATURE:
<221> NAME/KEY: misc_feature
<222> LOCATION: (1)..(22)
<223> OTHER INFORMATION: BAG3-based specific antisense oligonucleotide

<400> SEQUENCE: 11
attaaaggcg ggggtgacgt gg                                            22

<210> SEQ ID NO 12
<211> LENGTH: 27
<212> TYPE: DNA
<213> ORGANISM: Homo sapiens
<220> FEATURE:
<221> NAME/KEY: misc_feature
<222> LOCATION: (1)..(27)
<223> OTHER INFORMATION: BAG3-based specific control nonsense
      oligonucleotide

<400> SEQUENCE: 12
ttatattcta ttatatttat gaactcc                                       27
```

```
<210> SEQ ID NO 13
<211> LENGTH: 22
<212> TYPE: DNA
<213> ORGANISM: Homo sapiens
<220> FEATURE:
<221> NAME/KEY: misc_feature
<222> LOCATION: (1)..(22)
<223> OTHER INFORMATION: BAG3-based specific control nonsense
      oligonucleotide

<400> SEQUENCE: 13
cctcgtaacc accgacctca at                                              22

<210> SEQ ID NO 14
<211> LENGTH: 22
<212> TYPE: DNA
<213> ORGANISM: Homo sapiens
<220> FEATURE:
<221> NAME/KEY: misc_feature
<222> LOCATION: (1)..(22)
<223> OTHER INFORMATION: BAG3-based specific control nonsense
      oligonucleotide

<400> SEQUENCE: 14
gcttatggag gattgaggtt gg                                              22

<210> SEQ ID NO 15
<211> LENGTH: 16
<212> TYPE: PRT
<213> ORGANISM: Homo sapiens
<220> FEATURE:
<221> NAME/KEY: PEPTIDE
<222> LOCATION: (1)..(16)
<223> OTHER INFORMATION: BAG3-protein specific epitope

<400> SEQUENCE: 15

Asp Arg Asp Pro Leu Pro Pro Gly Trp Glu Ile Lys Ile Asp Pro Gln
1               5                   10                  15

<210> SEQ ID NO 16
<211> LENGTH: 15
<212> TYPE: PRT
<213> ORGANISM: Homo sapiens
<220> FEATURE:
<221> NAME/KEY: PEPTIDE
<222> LOCATION: (1)..(15)
<223> OTHER INFORMATION: BAG3-protein specific epitope

<400> SEQUENCE: 16

Ser Ser Pro Lys Ser Val Ala Thr Glu Glu Arg Ala Ala Pro Ser
1               5                   10                  15

<210> SEQ ID NO 17
<211> LENGTH: 15
<212> TYPE: PRT
<213> ORGANISM: Homo sapiens
<220> FEATURE:
<221> NAME/KEY: PEPTIDE
<222> LOCATION: (1)..(15)
<223> OTHER INFORMATION: BAG3-protein specific epitope

<400> SEQUENCE: 17

Asp Lys Gly Lys Lys Asn Ala Gly Asn Ala Glu Asp Pro His Thr
1               5                   10                  15

<210> SEQ ID NO 18
<211> LENGTH: 15
<212> TYPE: PRT
<213> ORGANISM: Homo sapiens
```

```
-continued

<220> FEATURE:
<221> NAME/KEY: PEPTIDE
<222> LOCATION: (1)..(15)
<223> OTHER INFORMATION: BAG3-protein specific epitope

<400> SEQUENCE: 18

Asn Pro Ser Ser Met Thr Asp Thr Pro Gly Asn Pro Ala Ala Pro
1               5                   10                  15
```